(12) United States Patent
Hawiger et al.

(10) Patent No.: US 11,364,278 B2
(45) Date of Patent: *Jun. 21, 2022

(54) COMPOSITIONS AND METHODS FOR TARGETING NUCLEAR IMPORT SHUTTLES AND TREATING INFLAMMATORY DISORDERS

(71) Applicant: VANDERBILT UNIVERSITY, Nashville, TN (US)

(72) Inventors: Jack J. Hawiger, Nashville, TN (US); Jozef Zienkiewicz, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 13 days.

This patent is subject to a terminal disclaimer.

(21) Appl. No.: 16/799,350

(22) Filed: Feb. 24, 2020

(65) Prior Publication Data

US 2020/0197482 A1 Jun. 25, 2020

Related U.S. Application Data

(62) Division of application No. 15/297,996, filed on Oct. 19, 2016, now Pat. No. 10,556,928, which is a division of application No. 14/251,135, filed on Apr. 11, 2014, now Pat. No. 9,492,544.

(60) Provisional application No. 61/810,939, filed on Apr. 11, 2013.

(51) Int. Cl.
| | |
|---|---|
| A61K 38/16 | (2006.01) |
| A61K 38/00 | (2006.01) |
| A61P 35/00 | (2006.01) |
| A61P 17/00 | (2006.01) |
| C07K 14/47 | (2006.01) |
| A61K 45/06 | (2006.01) |
| A61K 38/12 | (2006.01) |
| C07K 14/50 | (2006.01) |
| A61K 31/167 | (2006.01) |
| A61K 31/192 | (2006.01) |
| A61P 29/00 | (2006.01) |

(52) U.S. Cl.
CPC ............ *A61K 38/16* (2013.01); *A61K 31/167* (2013.01); *A61K 31/192* (2013.01); *A61K 38/12* (2013.01); *A61K 45/06* (2013.01); *A61P 29/00* (2018.01); *C07K 14/47* (2013.01); *C07K 14/4702* (2013.01); *C07K 14/50* (2013.01); *C07K 2319/00* (2013.01); *C07K 2319/09* (2013.01)

(58) Field of Classification Search
None
See application file for complete search history.

(56) References Cited

U.S. PATENT DOCUMENTS

| | | | |
|---|---|---|---|
| 5,807,746 A | 9/1998 | Lin et al. | |
| 6,043,339 A | 3/2000 | Lin et al. | |
| 6,495,518 B1 | 12/2002 | Hawiger et al. | |
| 6,624,146 B1 | 9/2003 | Imamura et al. | |
| 7,553,929 B2 | 6/2009 | Hawiger et al. | |
| 7,576,058 B1 | 8/2009 | Lin et al. | |
| 8,324,148 B2 | 12/2012 | Hawiger et al. | |
| 8,420,096 B2 | 4/2013 | Hawiger et al. | |
| 8,932,559 B2 | 1/2015 | Hawiger et al. | |
| 9,044,433 B2 | 6/2015 | Hawiger et al. | |
| 9,492,544 B2 * | 11/2016 | Hawiger ............... | A61K 31/192 |
| 2004/0258688 A1 | 12/2004 | Hawiger et al. | |
| 2010/0210534 A1 | 8/2010 | Bevec | |
| 2011/0229525 A1 | 9/2011 | Hawiger et al. | |
| 2021/0015893 A1* | 1/2021 | Hawiger ............... | A61K 31/167 |

FOREIGN PATENT DOCUMENTS

| | | |
|---|---|---|
| WO | 1999049879 | 10/1999 |
| WO | 2001037821 | 5/2001 |
| WO | 2009039996 | 4/2009 |
| WO | 2014086835 | 6/2014 |

OTHER PUBLICATIONS

U.S. Appl. No. 17/275,764, filed Mar. 2021, Hawiger; Jack J.*
Pramanick et al., Pharma Times 45:65-77 (Mar. 2013) (Year: 2013).*
Manoj, S., "Review on: The Pharmaceutical Packaging," available online at https://www.pharmatutor.org/articles/the-pharmaceutical-packaging-article, 78 pages (2011) (Year: 2011).*
Bhatia et al.: "Insulin Therapy for Patients With Type I Diabetes", Supplement of JAPI, vol. 55 (2007) pp. 29-40.
Butler et al.: "Beta-Cell Deficit and Increased Beta-Cell Apoptosis in Humans With Type-2 Diabetes", Diabetes, vol. 52 (2003) pp. 102-110.
Cingolani G, Petosa C, Weis K, Muller CW. Structure of importin-beta bound to the IBB domain of importin-alpha. Nature. May 20, 1999;399(6733):221-9.
Cingolani Gl, Bednenko J, Gillespie MT, Gerace L. Molecular basis for the recognition of a nonclassical nuclear localization signal by importin beta. Mol Cell. Dec. 2002;10(6):1345-53.
Dabek et al.: "Nuclear factor kappa-light-chain-enhancer of activated B cells (NF-kB): A new potential therapeutic target in atherosclerosis?", Pharmacological Reports (Sep. 1, 2010) 62(5):778-783.

(Continued)

*Primary Examiner* — Thea D' Ambrosio
(74) *Attorney, Agent, or Firm* — Meunier Carlin & Curfman LLC

(57) ABSTRACT

The present invention relates to compositions and methods for treating autoimmune, microbial, metabolic, neoplastic, and posttraumatic diseases mediated by inflammation in a subject. Compositions and methods including at least one importin beta-selective nuclear transport modifier (NTM) and/or at least one importin alpha-selective NTM, and/or at least one importin alpha-specific NTM, and/or at least one inhibitor of importin alpha and importin beta complex formation may be administered to a subject to modulate the transport of transcription factors, mediated by nuclear import adaptors, into the nucleus of a cell resulting in a decrease or abrogation of inflammation.

17 Claims, 12 Drawing Sheets

Specification includes a Sequence Listing.

(56) References Cited

OTHER PUBLICATIONS

Daewoong, et al. "Intracellular protein therapy with SOCS3 inhibits inflammation and apoptosis" Nature Medicine 11, 892-898 (2005).
Extended European Search Report completed on Mar. 18, 2015 in EP Application No. 12838976.4 (17 pages).
Fischer et al., ChemBioChem 6:2126-2142 (2005).
Görlich D, Henklein P, Laskey RA, Hartmann E. A 41 amino acid motif in importin-alpha confers binding to importin-beta and hence transit into the nucleus. EMBO J. Apr. 15, 1996;15(8):1810-7.
Greenblatt article, available online at http://drhellengreenblatt.info/archives/1688, 3 pages (2014).
Han et al.: "Reciprocal and coordinate regulation of serum amyloid A versus apolipoprotein A-I and paraoaonase-1 by inflammation in murine hepatocytes", Arteriosclerosis, Thrombosis, and Vascular Biology (Aug. 1, 2006) 26(8): 1806-1813.
Hawiger et al., "Cellular import of functional peptides to block intracellular signaling," Current Opinion in Immunology 9:189-196 (1997).
Hawiger, "Lipopolysaccharide-induced signal transduction and gene transcription." In Endotoxin and the Lungs, K. Brigham, ed., Marcel Dekker, Inc., New York, Basel, Hong Kong, pp. 69-82 (1994).
Hawiger, "Peptide/Protein Delivery," Encylopedia of Molecular Medicine 2435-2438 (2002).
Hawiger, J. "Innate immunity and inflammation: a transcriptional paradigm." Immunol Res 23, 99-109 (2001).
Hawiger, J. "Noninvasive Intracellular Delivery of Functional Peptides and Proteins" Curr. Opin. Chem. Biol. 3(1):89-94, Feb. 1999.
Hering et al.: "Single-Donor, Marginal-Dose Islet Transplantation in Patients With Type 1 Diabetes", Journal of the American Medical Society, vol. 293, No. 7 (2005) pp. 830-835.
Hui et al.: "The inhibitory effect of polypeptide cSN50 on alcoholic hepatic injuries through blocking the binding of NF-kappa B to importin alpha", Scandinavian Journal of Gastroenterology, (Jul. 1, 2011) 46(7-8): 931-940.
Jaggi et al.: "Modulation of Nuclear Pore Topology by Transport Modifiers", Biophysical Journal, vol. 84 (2003) pp. 665-670.
Kim et al., PNAS vol. 104(6):p. 1913-1918, 2007.
Kobe B., Autoinhibition by an internal nuclear localization signal revealed by the crystal structure of mammalian importin alpha. Nat Struct Biol. Apr. 1999;6(4):388-97.
Kosugi S, Hasebe M, Entani T, Takayama S, Tomita M, Yanagawa H. Design of peptide inhibitors for the importin alpha/beta nuclear import pathway by activity-based profiling. Chem Biol. Sep. 22, 2008;15(9):940-9. doi: 10.1016/j.chembiol.2008.07.019.
Kumar, Current Science Review, Issue 1, 9 pages (Jan. 1, 2015).
Lin et al.: "Inhibition of nuclear translocation of transcription factor NF-KB by a synthetic peptide containing a cell membrane-permeable motif and nuclear localization sequence", Journal of Biological Chemistry (Jun. 16, 1995) 270 (24):14255-14258.
Liu et al., "Nuclear Import of Proinflammatory Transcription Factors is Required for Massive Liver Apoptosis Induced by Bacterial Lipopolysaccharide", Journal of Biological Chemistry, vol. 279(46):p. 48434-48442, 2004.
Liu et al., "Peptide-directed Suppression of a Pro-inflammatory Cytokine Response," Journal of Biological Chemistry, Jun. 2, 2000 American Society for Biochemistry and Molecular Biology, vol. 275, Nr:22, pp. 16774-16778, (2000).
Liu et al.: "Suppression of Acute Lung Inflammation by Intracellular Peptide Delivery of a Nuclear Import Inhibitor", Molecular Therapy vol. 17(5):p. 796-802, 2009.
Liu, et al. "Identification of a functionally important sequence in the cytoplasmic tail of integrin beta 3 by using cell-permeable peptide analogs," Proceedings of the National Academy of Sciences, Oct. 1, 1996 National Academy of Sciences, vol. 93, pp. 11819-11824, (1996).
Lott K, Cingolani G., The importin β binding domain as a master regulator of nucleocytoplasmic transport. Biochim Biophys Acta. Sep. 2011;1813(9):1578-92. doi: 10.1016/j.bbamcr.2010.10.012. Epub Oct. 26, 2010.
Meier et al.: "Sustained Beta Cell Apoptosis in Patients With Long-Standing Type 1 Diabetes: Indirect Evidence for Islet Regeneration", Diabetologia, vol. 48 (2005) pp. 2221-2228.
Moore et al.: "In Viro Islet Protection by a Nuclear Import Inhibitor in a Mouse Model of Type 1 Diabetes", PLoS One p. 1-12, vol. 5 Issue 10, e13235, Oct. 2010.
Moore et al.: "Suppression of Type I Diabetes by Targeting Nuclear Import of Pro-Inflammatory Transcription Factors", Diabetes, vol. 56, Suppl. 1 (2007) pp. A58.
Moore JD, Yang J, Truant R, Kornbluth S., Nuclear import of Cdk/cyclin complexes: identification of distinct mechanisms for import of Cdk2/cyclin E and Cdc2/cyclin B1., J Cell Biol. Jan. 25, 1999;144(2):213-24.
Orange, J. S. et al.: "Cell penetrating peptide inhibitors of Nuclear Factor-kappa B", Cell. Mo!. Life Sci. 65, p. 3564-3591, 2008.
Pieper et al.: "Activation of Nuclear Factor-[kappa]B in Cultured Endothelial Cells by Increased Glucose Concentration: Prevention by Calphostin C", Journal of Cardiovascular Pharmacology vol. 30(4): p. 528-532, 1997.
Rizo et al., Annu. Rev. Biochem. 61:387-418 (1992).
Simpson et al., BMC Neurology 14:15 (2014).
Smith et al., Nursing, pp. 37-42 (2014).
Wajchenberg, B. L. "Beta-Cell Failure in Diabetes and Preservation by Clinical Treatment", Endocrine Reviews, vol. 28, No. 2 (2007) pp. 187-218.
Yang et al., Karyopherin alpha7 (KPNA7), a divergent member of the importin alpha family of nuclear import receptors. BMC Cell Biol. Aug. 11, 2010;11:63. doi: 10.1186/1471-2121-11-63.
Zhang et al. "Preparation of functionally active cell-permeable peptides by single-step ligation of two peptide modules" PNAS Aug. 4, 1998 vol. 95 No. 16 9184-9189.
Zienkiewicz et al.: "Targeting Nuclear Import Shuttles, Importins/Karyopherins alpha by a Peptide Mimicking the NF kB1/p50 Nuclear Localization Sequence", Journal of the American Heart Assoc. 2013;2:e000386; originally published Sep. 16, 2013.

* cited by examiner

A

B

SEQUENCE LISTING

```
<160> NUMBER OF SEQ ID NOS: 46

<210> SEQ ID NO 1
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Any amino acid
```

```
<220> FEATURE:
<221> NAME/KEY: MOD_RES
<222> LOCATION: (13)..(14)
<223> OTHER INFORMATION: Any amino acid
<220> FEATURE:
<223> OTHER INFORMATION: see specification as filed for detailed
      description of substitutions and preferred embodiments

<400> SEQUENCE: 1

Ala Ala Val Ala Leu Leu Pro Ala Val Xaa Leu Ala Xaa Xaa Ala Pro
1               5                   10                  15

Cys Val Gln Arg Lys Arg Gln Lys Leu Met Pro Cys
            20                  25

<210> SEQ ID NO 2
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Ala Val Ala Leu Leu Pro Ala Val Leu Leu Ala Leu Leu Ala Pro
1               5                   10                  15

Cys Val Gln Arg Asp Glu Gln Lys Leu Met Pro Cys
            20                  25

<210> SEQ ID NO 3
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Ala Val Ala Leu Leu Pro Ala Val Leu Leu Ala Leu Leu Ala Pro
1               5                   10                  15

Val Gln Arg Lys Arg Gln Lys Leu Met Pro
            20                  25

<210> SEQ ID NO 4
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Ala Val Ala Leu Leu Pro Ala Val Leu Leu Ala Leu Leu Ala Pro
1               5                   10                  15

Cys Tyr Val Gln Arg Lys Arg Gln Lys Leu Met Pro Cys
            20                  25

<210> SEQ ID NO 5
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Ala Val Ala Leu Leu Pro Ala Val Leu Leu Ala Leu Leu Ala Pro
```

Cys Val Gln Arg Lys Arg Gln Lys Leu Met Pro Cys
            20                  25

<210> SEQ ID NO 6
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Ala Val Ala Leu Leu Pro Ala Val Leu Leu Ala Leu Leu Ala Pro
1               5                   10                  15

Val Gln Arg Asp Glu Gln Lys Leu Met Pro
            20                  25

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Ala Val Ala Leu Leu Pro Ala Val Leu Leu Ala Leu Leu Ala Pro
1               5                   10                  15

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Val Gln Arg Asp Glu Gln Lys Leu Met Pro
1               5                   10

<210> SEQ ID NO 9
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Ala Ala Val Ala Leu Leu Pro Ala Val Leu Leu Ala Leu Leu Ala Pro
1               5                   10                  15

Arg Arg Arg Arg Ile Glu Val Asn Val Glu Leu Arg Lys Ala Lys Lys
            20                  25                  30

<210> SEQ ID NO 10
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Ala Ala Val Ala Leu Leu Pro Ala Val Leu Leu Ala Leu Leu Ala Pro

```
1               5                   10                  15
Arg Arg Arg Arg Ile Glu Val Asn Val Glu Leu Arg Lys Ala Lys Lys
            20                  25                  30

Asp Asp

<210> SEQ ID NO 11
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Ala Ala Val Ala Leu Leu Pro Ala Val Leu Leu Ala Leu Leu Ala Pro
1               5                   10                  15

Arg Arg Gln Arg Asn Glu Val Val Val Glu Leu Arg Lys Asn Lys Arg
            20                  25                  30

Asp Glu

<210> SEQ ID NO 12
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ala Ala Val Ala Leu Leu Pro Ala Val Leu Leu Ala Leu Leu Ala Pro
1               5                   10                  15

Arg Arg His Arg Asn Glu Val Thr Val Glu Leu Arg Lys Asn Lys Arg
            20                  25                  30

Asp Glu

<210> SEQ ID NO 13
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ala Ala Val Ala Leu Leu Pro Ala Val Leu Leu Ala Leu Leu Ala Pro
1               5                   10                  15

Arg Arg Arg Arg Glu Glu Glu Gly Leu Gln Leu Arg Lys Gln Lys Arg
            20                  25                  30

Glu Glu

<210> SEQ ID NO 14
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ala Ala Val Ala Leu Leu Pro Ala Val Leu Leu Ala Leu Leu Ala Pro
1               5                   10                  15

Arg Arg Arg Arg Glu Glu Glu Gly Ile Gln Leu Arg Lys Gln Lys Arg
```

-continued

```
                    20                  25                  30

Glu Gln

<210> SEQ ID NO 15
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Ala Val Ala Leu Leu Pro Ala Val Leu Leu Ala Leu Leu Ala Pro
1               5                   10                  15

Cys Thr Glu Met Arg Arg Arg Arg Ile Glu Val Cys
            20                  25

<210> SEQ ID NO 16
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Ala Ala Val Ala Leu Leu Pro Ala Val Leu Leu Ala Leu Leu Ala Pro
1               5                   10                  15

Val Glu Leu Arg Lys Ala Lys Lys Asp Asp Gln Met Leu Lys Arg Arg
            20                  25                  30

Asn Val Ser Ser Phe
        35

<210> SEQ ID NO 17
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Ala Ala Val Ala Leu Leu Pro Ala Val Leu Leu Ala Leu Leu Ala Pro
1               5                   10                  15

Val Glu Leu Arg Lys Asn Lys Arg Asp Glu His Leu Leu Lys Arg Arg
            20                  25                  30

Asn Val Pro His Glu
        35

<210> SEQ ID NO 18
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ala Ala Val Ala Leu Leu Pro Ala Val Leu Leu Ala Leu Leu Ala Pro
1               5                   10                  15

Val Glu Leu Arg Lys Asn Lys Arg Asp Glu His Leu Leu Lys Lys Arg
            20                  25                  30

Asn Val Pro Gln Glu
```

<210> SEQ ID NO 19
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ala Ala Val Ala Leu Leu Pro Ala Val Leu Leu Ala Leu Leu Ala Pro
1               5                   10                  15

Leu Gln Leu Arg Lys Gln Lys Arg Glu Glu Gln Leu Phe Lys Arg Arg
            20                  25                  30

Asn Val Ala Thr Ala
        35

<210> SEQ ID NO 20
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Ala Ala Val Ala Leu Leu Pro Ala Val Leu Leu Ala Leu Leu Ala Pro
1               5                   10                  15

Ile Gln Leu Arg Lys Gln Lys Arg Glu Gln Gln Leu Phe Lys Arg Arg
            20                  25                  30

Asn Val Glu Leu Ile
        35

<210> SEQ ID NO 21
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Ala Val Ala Leu Leu Pro Ala Val Leu Leu Ala Leu Leu Ala Pro
1               5                   10                  15

Cys Val Glu Leu Arg Lys Ala Lys Lys Asp Asp Gln Cys
            20                  25

<210> SEQ ID NO 22
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Ala Val Ala Leu Leu Pro Ala Val Leu Leu Ala Leu Leu Ala Pro
1               5                   10                  15

Cys Val Glu Leu Arg Lys Asn Lys Arg Asp Glu His Cys
            20                  25

<210> SEQ ID NO 23
<211> LENGTH: 29

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Ala Val Ala Leu Leu Pro Ala Val Leu Leu Ala Leu Leu Ala Pro
1               5                   10                  15

Cys Leu Gln Leu Arg Lys Gln Lys Arg Glu Glu Gln Cys
            20                  25

<210> SEQ ID NO 24
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Ala Val Ala Leu Leu Pro Ala Val Leu Leu Ala Leu Leu Ala Pro
1               5                   10                  15

Cys Ile Gln Leu Arg Lys Gln Lys Arg Glu Gln Gln Cys
            20                  25

<210> SEQ ID NO 25
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Ala Val Ala Leu Leu Pro Ala Val Leu Leu Ala Leu Leu Ala Pro
1               5                   10                  15

Cys Gln Met Leu Lys Arg Arg Asn Val Ser Ser Phe Cys
            20                  25

<210> SEQ ID NO 26
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ala Ala Val Ala Leu Leu Pro Ala Val Leu Leu Ala Leu Leu Ala Pro
1               5                   10                  15

Cys His Leu Leu Lys Arg Arg Asn Val Pro His Glu Cys
            20                  25

<210> SEQ ID NO 27
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ala Ala Val Ala Leu Leu Pro Ala Val Leu Leu Ala Leu Leu Ala Pro
1               5                   10                  15
```

Cys His Leu Leu Lys Lys Arg Asn Val Pro Gln Glu Cys
            20                  25

<210> SEQ ID NO 28
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ala Ala Val Ala Leu Leu Pro Ala Val Leu Leu Ala Leu Leu Ala Pro
1               5                   10                  15

Cys Gln Leu Phe Lys Arg Arg Asn Val Ala Thr Ala Cys
            20                  25

<210> SEQ ID NO 29
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ala Ala Val Ala Leu Leu Pro Ala Val Leu Leu Ala Leu Leu Ala Pro
1               5                   10                  15

Cys Gln Leu Phe Lys Arg Arg Asn Val Glu Leu Ile Cys
            20                  25

<210> SEQ ID NO 30
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (13)..(14)
<223> OTHER INFORMATION: Any amino acid
<220> FEATURE:
<223> OTHER INFORMATION: see specification as filed for detailed
      description of substitutions and preferred embodiments

<400> SEQUENCE: 30

Ala Ala Val Ala Leu Leu Pro Ala Val Xaa Leu Ala Xaa Xaa Ala Pro
1               5                   10                  15

Val Glu Leu Arg Lys Asn Lys Arg Asp Glu His Leu Leu Lys Arg Arg
            20                  25                  30

Asn Val Pro His Glu
        35

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gln Arg Lys Arg Gln Lys
1               5

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Arg Asp Glu Gln Lys
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Lys Lys Lys Arg Lys Val Glu
1               5

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Val Gln Arg Lys Arg Gln Lys Leu Met Pro
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Cys Val Gln Arg Lys Arg Gln Lys Leu Met Pro Cys
1               5                   10

<210> SEQ ID NO 36
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Val Glu Leu Arg Lys Ala Lys Lys Asp Asp Gln Met Leu Lys Arg Arg
1               5                   10                  15

Asn Val Ser Ser Phe
            20

<210> SEQ ID NO 37
<211> LENGTH: 21

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Val Glu Leu Arg Lys Asn Lys Arg Asp Glu His Leu Leu Lys Arg Arg
1               5                   10                  15

Asn Val Pro His Glu
            20

<210> SEQ ID NO 38
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Val Glu Leu Arg Lys Asn Lys Arg Asp Glu His Leu Leu Lys Lys Arg
1               5                   10                  15

Asn Val Pro Gln Glu
            20

<210> SEQ ID NO 39
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Leu Gln Leu Arg Lys Gln Lys Arg Glu Gln Leu Phe Lys Arg Arg
1               5                   10                  15

Asn Val Ala Thr Ala
            20

<210> SEQ ID NO 40
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ile Gln Leu Arg Lys Gln Lys Arg Glu Gln Gln Leu Phe Lys Arg Arg
1               5                   10                  15

Asn Val Glu Leu Ile
            20

<210> SEQ ID NO 41
<211> LENGTH: 520
<212> TYPE: PRT
<213> ORGANISM: Homo sapiens

<400> SEQUENCE: 41

Met Ser Thr Asn Glu Asn Ala Asn Thr Pro Ala Ala Arg Leu His Arg
1               5                   10                  15

Phe Lys Asn Lys Gly Lys Asp Ser Thr Glu Met Arg Arg Arg Ile
                20                  25                  30
```

-continued

```
Glu Val Asn Val Glu Leu Arg Lys Ala Lys Asp Asp Gln Met Leu
         35                  40                  45
Lys Arg Arg Asn Val Ser Ser Phe Pro Asp Asp Ala Thr Ser Pro Leu
 50                  55                  60
Gln Glu Asn Arg Asn Asn Gln Gly Thr Val Asn Trp Ser Val Asp Asp
 65                  70                  75                  80
Ile Val Lys Gly Ile Asn Ser Ser Asn Val Glu Asn Gln Leu Gln Ala
                 85                  90                  95
Thr Gln Ala Ala Arg Lys Leu Leu Ser Arg Glu Lys Gln Pro Pro Ile
                100                 105                 110
Asp Asn Ile Ile Arg Ala Gly Leu Ile Pro Lys Phe Val Ser Phe Leu
            115                 120                 125
Gly Arg Thr Asp Cys Ser Pro Ile Gln Phe Glu Ser Ala Trp Ala Leu
130                 135                 140
Thr Asn Ile Ala Ser Gly Thr Ser Glu Gln Thr Lys Ala Val Val Asp
145                 150                 155                 160
Gly Gly Ala Ile Arg Ala Phe Ile Ser Leu Leu Ala Ser Pro His Ala
                165                 170                 175
His Ile Ser Glu Gln Asp Val Trp Ala Leu Gly Asn Ile Ala Gly Asp
            180                 185                 190
Gly Ser Val Phe Arg Asp Leu Val Ile Lys Tyr Gly Ala Val Asp Pro
        195                 200                 205
Leu Leu Ala Leu Leu Ala Val Pro Asp Met Ser Ser Leu Ala Cys Gly
210                 215                 220
Tyr Leu Arg Asn Leu Thr Trp Thr Leu Ser Asn Leu Cys Arg Asn Lys
225                 230                 235                 240
Asn Pro Ala Pro Pro Ile Asp Ala Val Glu Gln Ile Leu Pro Thr Leu
                245                 250                 255
Val Arg Leu Leu His His Asp Asp Pro Glu Val Leu Ala Asp Thr Cys
            260                 265                 270
Trp Ala Ile Ser Tyr Leu Thr Asp Gly Pro Asn Glu Arg Ile Gly Met
        275                 280                 285
Val Val Lys Thr Gly Val Val Pro Gln Leu Val Lys Leu Leu Gly Ala
290                 295                 300
Ser Glu Leu Pro Ile Val Thr Pro Ala Leu Arg Ala Ile Gly Asn Ile
305                 310                 315                 320
Val Thr Gly Thr Asp Glu Gln Thr Gln Val Val Ile Asp Ala Gly Ala
                325                 330                 335
Leu Ala Val Phe Pro Ser Leu Leu Thr Asn Pro Lys Thr Asn Ile Gln
            340                 345                 350
Lys Glu Ala Thr Trp Thr Met Ser Asn Ile Thr Ala Gly Arg Gln Asp
        355                 360                 365
Gln Ile Gln Gln Val Val Asn His Gly Leu Val Pro Phe Leu Val Ser
370                 375                 380
Val Leu Ser Lys Ala Asp Phe Lys Thr Gln Lys Glu Ala Val Trp Ala
385                 390                 395                 400
Val Thr Asn Tyr Thr Ser Gly Gly Thr Val Glu Gln Ile Val Tyr Leu
                405                 410                 415
Val His Cys Gly Ile Ile Glu Pro Leu Met Asn Leu Leu Thr Ala Lys
            420                 425                 430
Asp Thr Lys Ile Ile Leu Val Ile Leu Asp Ala Ile Ser Asn Ile Phe
        435                 440                 445
Gln Ala Ala Glu Lys Leu Gly Glu Thr Glu Lys Leu Ser Ile Met Ile
```

450                 455                 460
Glu Glu Cys Gly Gly Leu Asp Lys Ile Glu Ala Leu Gln Asn His Glu
465                 470                 475                 480

Asn Glu Ser Val Tyr Lys Ala Ser Leu Ser Leu Ile Glu Lys Tyr Phe
                485                 490                 495

Ser Val Glu Glu Glu Asp Gln Asn Val Val Pro Glu Thr Thr Ser
            500                 505                 510

Glu Gly Tyr Thr Phe Gln Val Gln
            515                 520

<210> SEQ ID NO 42
<211> LENGTH: 512
<212> TYPE: PRT
<213> ORGANISM: Homo sapiens

<400> SEQUENCE: 42

Met Ala Asp Asn Glu Lys Leu Asp Asn Gln Arg Leu Lys Asn Phe Lys
1               5                   10                  15

Asn Lys Gly Arg Asp Leu Glu Thr Met Arg Arg Gln Arg Asn Glu Val
                20                  25                  30

Val Val Glu Leu Arg Lys Asn Lys Arg Asp Glu His Leu Leu Lys Arg
            35                  40                  45

Arg Asn Val Pro His Glu Asp Ile Cys Glu Asp Ser Asp Ile Asp Gly
50                  55                  60

Asp Tyr Arg Val Gln Asn Thr Ser Leu Glu Ala Ile Val Gln Asn Ala
65                  70                  75                  80

Ser Ser Asp Asn Gln Gly Ile Gln Leu Ser Ala Val Gln Ala Ala Arg
                85                  90                  95

Lys Leu Leu Ser Ser Asp Arg Asn Pro Pro Ile Asp Asp Leu Ile Lys
            100                 105                 110

Ser Gly Ile Leu Pro Ile Leu Val His Cys Leu Glu Arg Asp Asp Asn
        115                 120                 125

Pro Ser Leu Gln Phe Glu Ala Ala Trp Ala Leu Thr Asn Ile Ala Ser
130                 135                 140

Gly Thr Ser Glu Gln Thr Gln Ala Val Val Gln Ser Asn Ala Val Pro
145                 150                 155                 160

Leu Phe Leu Arg Leu Leu His Ser Pro His Gln Asn Val Cys Glu Gln
                165                 170                 175

Ala Val Trp Ala Leu Gly Asn Ile Ile Gly Asp Gly Pro Gln Cys Arg
            180                 185                 190

Asp Tyr Val Ile Ser Leu Gly Val Val Lys Pro Leu Leu Ser Phe Ile
        195                 200                 205

Ser Pro Ser Ile Pro Ile Thr Phe Leu Arg Asn Val Thr Trp Val Met
210                 215                 220

Val Asn Leu Cys Arg His Lys Asp Pro Pro Pro Met Glu Thr Ile
225                 230                 235                 240

Gln Glu Ile Leu Pro Ala Leu Cys Val Leu Ile His His Thr Asp Val
                245                 250                 255

Asn Ile Leu Val Asp Thr Val Trp Ala Leu Ser Tyr Leu Thr Asp Ala
            260                 265                 270

Gly Asn Glu Gln Ile Gln Met Val Ile Asp Ser Gly Ile Val Pro His
        275                 280                 285

Leu Val Pro Leu Leu Ser His Gln Glu Val Lys Val Gln Thr Ala Ala
290                 295                 300

```
Leu Arg Ala Val Gly Asn Ile Val Thr Gly Thr Asp Glu Gln Thr Gln
305                 310                 315                 320

Val Val Leu Asn Cys Asp Ala Leu Ser His Phe Pro Ala Leu Leu Thr
                325                 330                 335

His Pro Lys Glu Lys Ile Asn Lys Glu Ala Val Trp Phe Leu Ser Asn
            340                 345                 350

Ile Thr Ala Gly Asn Gln Gln Val Gln Ala Val Ile Asp Ala Asn
        355                 360                 365

Leu Val Pro Met Ile Ile His Leu Leu Asp Lys Gly Asp Phe Gly Thr
    370                 375                 380

Gln Lys Glu Ala Ala Trp Ala Ile Ser Asn Leu Thr Ile Ser Gly Arg
385                 390                 395                 400

Lys Asp Gln Val Ala Tyr Leu Ile Gln Gln Asn Val Ile Pro Pro Phe
                405                 410                 415

Cys Asn Leu Leu Thr Val Lys Asp Ala Gln Val Val Gln Val Val Leu
                420                 425                 430

Asp Gly Leu Ser Asn Ile Leu Lys Met Ala Glu Asp Glu Ala Glu Thr
            435                 440                 445

Ile Gly Asn Leu Ile Glu Glu Cys Gly Gly Leu Glu Lys Ile Glu Gln
450                 455                 460

Leu Gln Asn His Glu Asn Glu Asp Ile Tyr Lys Leu Ala Tyr Glu Ile
465                 470                 475                 480

Ile Asp Gln Phe Phe Ser Ser Asp Asp Ile Asp Glu Asp Pro Ser Leu
                485                 490                 495

Val Pro Glu Ala Ile Gln Gly Gly Thr Phe Gly Phe Asn Ser Ser Ala
            500                 505                 510
```

<210> SEQ ID NO 43
<211> LENGTH: 512
<212> TYPE: PRT
<213> ORGANISM: Homo sapiens

<400> SEQUENCE: 43

```
Met Ala Glu Asn Pro Ser Leu Glu Asn His Arg Ile Lys Ser Phe Lys
1               5                   10                  15

Asn Lys Gly Arg Asp Val Glu Thr Met Arg Arg His Arg Asn Glu Val
                20                  25                  30

Thr Val Glu Leu Arg Lys Asn Lys Arg Asp Glu His Leu Leu Lys Lys
            35                  40                  45

Arg Asn Val Pro Gln Glu Glu Ser Leu Glu Asp Ser Asp Val Asp Ala
50                  55                  60

Asp Phe Lys Ala Gln Asn Val Thr Leu Glu Ala Ile Leu Gln Asn Ala
65                  70                  75                  80

Thr Ser Asp Asn Pro Val Val Gln Leu Ser Ala Val Gln Ala Ala Arg
                85                  90                  95

Lys Leu Leu Ser Ser Asp Arg Asn Pro Pro Ile Asp Asp Leu Ile Lys
            100                 105                 110

Ser Gly Ile Leu Pro Ile Leu Val Lys Cys Leu Glu Arg Asp Asp Asn
        115                 120                 125

Pro Ser Leu Gln Phe Glu Ala Ala Trp Ala Leu Thr Asn Ile Ala Ser
    130                 135                 140

Gly Thr Ser Ala Gln Thr Gln Ala Val Val Gln Ser Asn Ala Val Pro
145                 150                 155                 160

Leu Phe Leu Arg Leu Leu Arg Ser Pro His Gln Asn Val Cys Glu Gln
                165                 170                 175
```

Ala Val Trp Ala Leu Gly Asn Ile Ile Gly Asp Gly Pro Gln Cys Arg
            180                 185                 190

Asp Tyr Val Ile Ser Leu Gly Val Val Lys Pro Leu Leu Ser Phe Ile
            195                 200                 205

Ser Pro Ser Ile Pro Ile Thr Phe Leu Arg Asn Val Thr Trp Val Ile
            210                 215                 220

Val Asn Leu Cys Arg Asn Lys Asp Pro Pro Pro Met Glu Thr Val
225                 230                 235                 240

Gln Glu Ile Leu Pro Ala Leu Cys Val Leu Ile Tyr His Thr Asp Ile
                245                 250                 255

Asn Ile Leu Val Asp Thr Val Trp Ala Leu Ser Tyr Leu Thr Asp Gly
            260                 265                 270

Gly Asn Glu Gln Ile Gln Met Val Ile Asp Ser Gly Val Val Pro Phe
            275                 280                 285

Leu Val Pro Leu Leu Ser His Gln Glu Val Lys Val Gln Thr Ala Ala
            290                 295                 300

Leu Arg Ala Val Gly Asn Ile Val Thr Gly Thr Asp Glu Gln Thr Gln
305                 310                 315                 320

Val Val Leu Asn Cys Asp Val Leu Ser His Phe Pro Asn Leu Leu Ser
                325                 330                 335

His Pro Lys Glu Lys Ile Asn Lys Glu Ala Val Trp Phe Leu Ser Asn
            340                 345                 350

Ile Thr Ala Gly Asn Gln Gln Gln Val Gln Ala Val Ile Asp Ala Gly
            355                 360                 365

Leu Ile Pro Met Ile Ile His Gln Leu Ala Lys Gly Asp Phe Gly Thr
            370                 375                 380

Gln Lys Glu Ala Ala Trp Ala Ile Ser Asn Leu Thr Ile Ser Gly Arg
385                 390                 395                 400

Lys Asp Gln Val Glu Tyr Leu Val Gln Asn Val Ile Pro Pro Phe
            405                 410                 415

Cys Asn Leu Leu Ser Val Lys Asp Ser Gln Val Val Gln Val Val Leu
            420                 425                 430

Asp Gly Leu Lys Asn Ile Leu Ile Met Ala Gly Asp Glu Ala Ser Thr
            435                 440                 445

Ile Ala Glu Ile Ile Glu Glu Cys Gly Gly Leu Glu Lys Ile Glu Val
450                 455                 460

Leu Gln Gln His Glu Asn Glu Asp Ile Tyr Lys Leu Ala Phe Glu Ile
465                 470                 475                 480

Ile Asp Gln Tyr Phe Ser Gly Asp Ile Asp Glu Asp Pro Cys Leu
                485                 490                 495

Ile Pro Glu Ala Thr Gln Gly Gly Thr Tyr Asn Phe Asp Pro Thr Ala
            500                 505                 510

<210> SEQ ID NO 44
<211> LENGTH: 529
<212> TYPE: PRT
<213> ORGANISM: Homo sapiens

<400> SEQUENCE: 44

Met Thr Thr Pro Gly Lys Glu Asn Phe Arg Leu Lys Ser Tyr Lys Asn
1               5                   10                  15

Lys Ser Leu Asn Pro Asp Glu Met Arg Arg Arg Arg Glu Glu Glu Gly
            20                  25                  30

Leu Gln Leu Arg Lys Gln Lys Arg Glu Glu Gln Leu Phe Lys Arg Arg

```
            35                  40                  45
Asn Val Ala Thr Ala Glu Glu Thr Glu Glu Val Met Ser Asp
             50                  55                  60
Gly Gly Phe His Glu Ala Gln Ile Asn Asn Met Glu Met Ala Pro Gly
 65                  70                  75                  80
Gly Val Ile Thr Ser Asp Met Ile Glu Met Ile Phe Ser Lys Ser Pro
                     85                  90                  95
Glu Gln Gln Leu Ser Ala Thr Gln Lys Phe Arg Lys Leu Leu Ser Lys
                100                 105                 110
Glu Pro Asn Pro Pro Ile Asp Glu Val Ile Ser Thr Pro Gly Val Val
            115                 120                 125
Ala Arg Phe Val Glu Phe Leu Lys Arg Lys Glu Asn Cys Thr Leu Gln
            130                 135                 140
Phe Glu Ser Ala Trp Val Leu Thr Asn Ile Ala Ser Gly Asn Ser Leu
145                 150                 155                 160
Gln Thr Arg Ile Val Ile Gln Ala Gly Ala Val Pro Ile Phe Ile Glu
                    165                 170                 175
Leu Leu Ser Ser Glu Phe Glu Asp Val Gln Glu Gln Ala Val Trp Ala
                180                 185                 190
Leu Gly Asn Ile Ala Gly Asp Ser Thr Met Cys Arg Asp Tyr Val Leu
            195                 200                 205
Asp Cys Asn Ile Leu Pro Pro Leu Leu Gln Leu Phe Ser Lys Gln Asn
    210                 215                 220
Arg Leu Thr Met Thr Arg Asn Ala Val Trp Ala Leu Ser Asn Leu Cys
225                 230                 235                 240
Arg Gly Lys Ser Pro Pro Pro Glu Phe Ala Lys Val Ser Pro Cys Leu
                    245                 250                 255
Asn Val Leu Ser Trp Leu Leu Phe Val Ser Asp Thr Asp Val Leu Ala
                260                 265                 270
Asp Ala Cys Trp Ala Leu Ser Tyr Leu Ser Asp Gly Pro Asn Asp Lys
            275                 280                 285
Ile Gln Ala Val Ile Asp Ala Gly Val Cys Arg Arg Leu Val Glu Leu
    290                 295                 300
Leu Met His Asn Asp Tyr Lys Val Val Ser Pro Ala Leu Arg Ala Val
305                 310                 315                 320
Gly Asn Ile Val Thr Gly Asp Asp Ile Gln Thr Gln Val Ile Leu Asn
                    325                 330                 335
Cys Ser Ala Leu Gln Ser Leu Leu His Leu Leu Ser Ser Pro Lys Glu
                340                 345                 350
Ser Ile Lys Lys Glu Ala Cys Trp Thr Ile Ser Asn Ile Thr Ala Gly
            355                 360                 365
Asn Arg Ala Gln Ile Gln Thr Val Ile Asp Ala Asn Ile Phe Pro Ala
    370                 375                 380
Leu Ile Ser Ile Leu Gln Thr Ala Glu Phe Arg Thr Arg Lys Glu Ala
385                 390                 395                 400
Ala Trp Ala Ile Thr Asn Ala Thr Ser Gly Gly Ser Ala Glu Gln Ile
                    405                 410                 415
Lys Tyr Leu Val Glu Leu Gly Cys Ile Lys Pro Leu Cys Asp Leu Leu
                420                 425                 430
Thr Val Met Asp Ser Lys Ile Val Gln Val Ala Leu Asn Gly Leu Glu
            435                 440                 445
Asn Ile Leu Arg Leu Gly Glu Gln Glu Ala Lys Arg Asn Gly Thr Gly
    450                 455                 460
```

```
Ile Asn Pro Tyr Cys Ala Leu Ile Glu Glu Ala Tyr Gly Leu Asp Lys
465                 470                 475                 480

Ile Glu Phe Leu Gln Ser His Glu Asn Gln Glu Ile Tyr Gln Lys Ala
            485                 490                 495

Phe Asp Leu Ile Glu His Tyr Phe Gly Thr Glu Asp Asp Ser Ser
        500                 505                 510

Ile Ala Pro Gln Val Asp Leu Asn Gln Gln Tyr Ile Phe Gln Gln
    515                 520                 525

Cys

<210> SEQ ID NO 45
<211> LENGTH: 527
<212> TYPE: PRT
<213> ORGANISM: Homo sapiens

<400> SEQUENCE: 45

Met Ala Ser Pro Gly Lys Asp Asn Tyr Arg Met Lys Ser Tyr Lys Asn
1               5                   10                  15

Lys Ala Leu Asn Pro Gln Glu Met Arg Arg Arg Glu Glu Glu Gly
            20                  25                  30

Ile Gln Leu Arg Lys Gln Lys Arg Glu Glu Gln Leu Phe Lys Arg Arg
            35                  40                  45

Asn Val Tyr Leu Pro Arg Asn Asp Glu Ser Met Leu Glu Ser Pro Ile
50                  55                  60

Gln Asp Ser Asp Ile Ser Ser Thr Val Pro Ile Pro Glu Glu Gly Val
65                  70                  75                  80

Val Thr Thr Asp Met Val Gln Met Ile Phe Ser Asn Asn Ala Asp Gln
                85                  90                  95

Gln Leu Thr Ala Thr Gln Lys Phe Arg Lys Leu Leu Ser Lys Glu Pro
            100                 105                 110

Asn Pro Pro Ile Asp Gln Val Ile Gln Lys Pro Gly Val Val Gln Arg
        115                 120                 125

Phe Val Lys Phe Leu Glu Arg Asn Glu Asn Cys Thr Leu Gln Phe Glu
    130                 135                 140

Ala Ala Trp Ala Leu Thr Asn Ile Ala Ser Gly Thr Phe Leu His Thr
145                 150                 155                 160

Lys Val Val Ile Glu Thr Gly Ala Val Pro Ile Phe Ile Lys Leu Leu
                165                 170                 175

Asn Ser Glu His Glu Asp Val Gln Glu Gln Ala Val Trp Ala Leu Gly
            180                 185                 190

Asn Ile Ala Gly Asp Asn Ala Glu Cys Arg Asp Phe Val Leu Asn Cys
        195                 200                 205

Glu Ile Leu Pro Pro Leu Glu Leu Leu Thr Asn Ser Asn Arg Leu
    210                 215                 220

Thr Thr Thr Arg Asn Ala Val Trp Ala Leu Ser Asn Leu Cys Arg Gly
225                 230                 235                 240

Lys Asn Pro Pro Pro Asn Phe Ser Lys Val Ser Pro Cys Leu Asn Val
                245                 250                 255

Leu Ser Arg Leu Leu Phe Ser Asp Pro Asp Val Leu Ala Asp Val
            260                 265                 270

Cys Trp Ala Leu Ser Tyr Leu Ser Asp Gly Pro Asn Asp Lys Ile Gln
        275                 280                 285

Ala Val Ile Asp Ser Gly Val Cys Arg Arg Leu Val Glu Leu Leu Met
    290                 295                 300
```

His Asn Asp Tyr Lys Val Val Ser Pro Ala Leu Arg Ala Val Gly Asn
305                 310                 315                 320

Ile Val Thr Gly Asp Asp Ile Gln Thr Gln Val Ile Leu Asn Cys Ser
                325                 330                 335

Ala Leu Pro Cys Leu Leu His Leu Leu Ser Ser Pro Lys Glu Ser Ile
            340                 345                 350

Arg Lys Glu Ala Cys Trp Thr Val Ser Asn Ile Thr Ala Gly Asn Arg
        355                 360                 365

Ala Gln Ile Gln Ala Val Ile Asp Ala Asn Ile Phe Pro Val Leu Ile
    370                 375                 380

Glu Ile Leu Gln Lys Ala Glu Phe Arg Thr Arg Lys Glu Ala Ala Trp
385                 390                 395                 400

Ala Ile Thr Asn Ala Thr Ser Gly Gly Thr Pro Glu Gln Ile Arg Tyr
                405                 410                 415

Leu Val Ala Leu Gly Cys Ile Lys Pro Leu Cys Asp Leu Leu Thr Val
            420                 425                 430

Met Asp Ser Lys Ile Val Gln Val Ala Leu Asn Gly Leu Glu Asn Ile
        435                 440                 445

Leu Arg Leu Gly Glu Gln Glu Ser Lys Gln Asn Gly Ile Gly Ile Asn
    450                 455                 460

Pro Tyr Cys Ala Leu Ile Glu Glu Ala Tyr Gly Leu Asp Lys Ile Glu
465                 470                 475                 480

Phe Leu Gln Ser His Glu Asn Gln Glu Ile Tyr Gln Lys Ala Phe Asp
                485                 490                 495

Leu Ile Glu His Tyr Phe Gly Val Glu Glu Asp Pro Ser Ile Val
            500                 505                 510

Pro Gln Val Asp Glu Asn Gln Gln Gln Phe Ile Phe Gln Gln Gln
        515                 520                 525

<210> SEQ ID NO 46
<211> LENGTH: 527
<212> TYPE: PRT
<213> ORGANISM: Homo sapiens

<400> SEQUENCE: 46

Met Glu Thr Met Ala Ser Pro Gly Lys Asp Asn Tyr Arg Met Lys Ser
1               5                   10                  15

Tyr Lys Asn Asn Ala Leu Asn Pro Glu Glu Met Arg Arg Arg Arg Glu
                20                  25                  30

Glu Glu Gly Ile Gln Leu Arg Lys Gln Lys Arg Glu Gln Gln Leu Phe
            35                  40                  45

Lys Arg Arg Asn Val Glu Leu Ile Asn Glu Glu Ala Ala Met Phe Asp
        50                  55                  60

Ser Leu Leu Met Asp Ser Tyr Val Ser Ser Thr Gly Glu Ser Val
65              70                  75                  80

Ile Thr Arg Glu Met Val Glu Met Leu Phe Ser Asp Asp Ser Asp Leu
                85                  90                  95

Gln Leu Ala Thr Thr Gln Lys Phe Arg Lys Leu Leu Ser Lys Glu Pro
            100                 105                 110

Ser Pro Pro Ile Asp Glu Val Ile Asn Thr Pro Arg Val Val Asp Arg
        115                 120                 125

Phe Val Glu Phe Leu Lys Arg Asn Glu Asn Cys Thr Leu Gln Phe Glu
    130                 135                 140

Ala Ala Trp Ala Leu Thr Asn Ile Ala Ser Gly Thr Ser Gln Gln Thr

-continued

```
            145                 150                 155                 160
Lys Ile Val Ile Glu Ala Gly Ala Val Pro Ile Phe Ile Glu Leu Leu
                    165                 170                 175

Asn Ser Asp Phe Glu Asp Val Gln Glu Gln Ala Val Trp Ala Leu Gly
                    180                 185                 190

Asn Ile Ala Gly Asp Ser Ser Val Cys Arg Asp Tyr Val Leu Asn Cys
                    195                 200                 205

Ser Ile Leu Asn Pro Leu Leu Thr Leu Thr Lys Ser Thr Arg Leu
                    210                 215                 220

Thr Met Thr Arg Asn Ala Val Trp Ala Leu Ser Asn Leu Cys Arg Gly
225                 230                 235                 240

Lys Asn Pro Pro Glu Phe Ala Lys Val Ser Pro Cys Leu Pro Val
                    245                 250                 255

Leu Ser Arg Leu Leu Phe Ser Ser Asp Ser Asp Leu Leu Ala Asp Ala
                    260                 265                 270

Cys Trp Ala Leu Ser Tyr Leu Ser Asp Gly Pro Asn Glu Lys Ile Gln
                    275                 280                 285

Ala Val Ile Asp Ser Gly Val Cys Arg Arg Leu Val Glu Leu Leu Met
                    290                 295                 300

His Asn Asp Tyr Lys Val Ala Ser Pro Ala Leu Arg Ala Val Gly Asn
305                 310                 315                 320

Ile Val Thr Gly Asp Asp Ile Gln Thr Gln Val Ile Leu Asn Cys Ser
                    325                 330                 335

Ala Leu Pro Cys Leu Leu His Leu Leu Ser Ser Pro Lys Glu Ser Ile
                    340                 345                 350

Arg Lys Glu Ala Cys Trp Thr Ile Ser Asn Ile Thr Ala Gly Asn Arg
                    355                 360                 365

Ala Gln Ile Gln Ala Val Ile Asp Ala Asn Ile Phe Pro Val Leu Ile
                    370                 375                 380

Glu Ile Leu Gln Lys Ala Glu Phe Arg Thr Arg Lys Glu Ala Ala Trp
385                 390                 395                 400

Ala Ile Thr Asn Ala Thr Ser Gly Gly Thr Pro Glu Gln Ile Arg Tyr
                    405                 410                 415

Leu Val Ser Leu Gly Cys Ile Lys Pro Leu Cys Asp Leu Leu Thr Val
                    420                 425                 430

Met Asp Ser Lys Ile Val Gln Val Ala Leu Asn Gly Leu Glu Asn Ile
                    435                 440                 445

Leu Arg Leu Gly Glu Gln Glu Gly Lys Arg Ser Gly Ser Gly Val Asn
                    450                 455                 460

Pro Tyr Cys Gly Leu Ile Glu Glu Ala Tyr Gly Leu Asp Lys Ile Glu
465                 470                 475                 480

Phe Leu Gln Ser His Glu Asn Gln Glu Ile Tyr Gln Lys Ala Phe Asp
                    485                 490                 495

Leu Ile Glu His Tyr Phe Gly Val Glu Asp Asp Ser Ser Leu Ala
                    500                 505                 510

Pro Gln Val Asp Glu Thr Gln Gln Phe Ile Phe Gln Gln Pro
                    515                 520                 525
```

COMPOSITIONS AND METHODS FOR TARGETING NUCLEAR IMPORT SHUTTLES AND TREATING INFLAMMATORY DISORDERS

CROSS REFERENCE TO RELATED APPLICATIONS

This application is a divisional of and claims priority to U.S. application Ser. No. 15/297,996, filed on Oct. 19, 2016, which is a divisional of U.S. application Ser. No. 14/251,135, filed on Apr. 11, 2014, now U.S. Pat. No. 9,492,544, which claims the benefit of U.S. provisional application No. 61/810,939, filed Apr. 11, 2013, applications which are incorporated herein by reference in its entirety.

STATEMENT REGARDING FEDERALLY SPONSORED RESEARCH OR DEVELOPMENT

This invention was made with government support under Grant Nos. HL085833 and AA015752 awarded by the National Institutes of Health. The U.S. government has certain rights in the invention.

SEQUENCE LISTING

The instant application contains a Sequence Listing which has been submitted electronically in ASCII format and is hereby incorporated by reference in its entirety. Said ASCII copy, created on Apr. 11, 2014, is named 20004-0161_SL.txt and is 42,791 bytes in size.

FIELD

The invention relates generally to the fields of biochemistry, cell biology, immunology, pharmacology and medicine.

BACKGROUND

Millions of people in the United States and globally suffer from inflammatory diseases Inflammation is the body's response to harmful stimuli, and when limited, is beneficial and helps the body heal. However, when inflammation is unchecked it can lead to tissue destruction, necrosis, and fibrosis. Similarly, autoimmune responses to a body's own cells and organs develop into rampant inflammation, destroying skin and joints in psoriasis, lupus, and rheumatoid arthritis, and insulin-producing beta cells in Type I diabetes. Microbial and metabolic inflammation leads to insulin resistance, which underlies Type 2 diabetes. Thus, one can distinguish conceptually between microbial inflammation as the mechanism of diseases caused by bacteria, viruses, and fungi, and autoimmune inflammation as the mechanism of diseases caused by emergence of autoreactive T and B lymphocytes and autoantibodies, and metabolic inflammation as the mechanism of diseases caused by excessive accumulation of metabolites (e.g. cholesterol esters, uric acid) due to inborn or acquired metabolic dysfunction. Chronic microbial inflammation caused by the oral microbiome of periodontitis, and bronchitis contribute to coronary heart disease while Hepatitis C virus infecting 200 million people worldwide contributes to fatty liver (steatosis), cirrhosis and, ultimately liver cancer (Jousilahti P, Salomaa V, Rasi V, Vahtera E Symptoms of chronic bronchitis, haemostatic factors, and coronary heart disease risk Atherosclerosis. 1999; 142(2):403-7 Epub 1999/02/25. PubMed PMID: 10030392, Khan M, Jahan S. Khaliq S, Ijaz B. Ahmad W, Samreen B, Hassan S. Interaction of the hepatitis C virus (HCV) core with cellular genes in the development of HCV-induced steatosis. Archives of virology. 2010; 155(11): 1735-53. Epub 2010/09/16. doi 10.1007/s00705-010-0797-7. PubMed PMID: 20842391.) These three distinct forms of inflammation (microbial, autoimmune, and metabolic) evolve from the innate immune response vested in Toll-like receptors (TLRs) that sense microbial and metabolic products and act in combination with one or more intracellular adaptors that belong to the MyD88 family (O'Neill L A. Bowie A G. The family of five: TIR-domain-containing adaptors in Toll-like receptor signalling. Nature reviews Immunology. 2007, 7(5):353-64 Epub 2007/04/26 doi: 10.1038/nri2079. PubMed PMID 17457343.) to mobilize signal transducers. Intracellular signaling complexes are formed to dispatch stress-responsive transcription factors (SRTFs) to the nucleus (Hawiger J. Innate immunity and inflammation: a transcriptional paradigm. Immunologic research.2001; 23(2-3):99-109 Epub 2001/07/11. doi: 10.1385/IR:23:2-3:099. PubMed PMID:11444396.), a process carried out by nuclear transport adaptors ("shuttles"), importins/karyopherins alpha and beta (importins α and β). The genomic response to proinflammatory insults is regulated by SRTFs, either alone or in various combinations (Hawiger J. Innate immunity and inflammation: a transcriptional paradigm Immunologic research.2001; 23(2-3):99-109. Epub 2001/07/11. doi: 10.1385/IR:232-3:099. PubMed PMID: 11444396.). Several key SRTFs, such as nuclear factor kappa B (NF-κB), activator protein 1 (AP-1), nuclear factor of activated T-cells (NFAT) and signal transducer and activator of transcription 1 (STAT1), contain one or more unique nuclear localization sequences (NLSs) arranged as monopartitc or bipartite motifs consisting of short sequences of basic residues (lysine and arginine) flanked by proline, valine or other non-polar amino acids that bind to importins α following cell activation (Weis K. Regulating access to the genome: nucleocytoplasmic transport throughout the cell cycle. Cell. 2003; 112(4) 441-51. Kpub 2003/02/26. PubMed PMID: 12600309.) These SRTFs in particular have been shown to play roles in immunity and inflammation and their dysregulation has been demonstrated in many autoimmune diseases, including systemic lupus erythematosus (SLE) (Gomez-Martin D, Diaz-Zamudio M, Crispin J C. Alcocer-Varcla J Interleukin 2 and systemic lupuserythematosus: beyond the transcriptional regulatory net abnormalities. Autoimmunity reviews.2009; 9(1) 34-9.Epub 2009/03/10. doi. 10.1016/j.autrev.2009.02.035. PubMed PMID: 19269352.) Importins α form heterodimers with importin β to facilitate docking to nuclear pores and ferry the SRTF cargo to the nucleus. Once inside the nucleus, transcription factors (TFs) are freed to bind their cognate promoters and initiate gene transcription, leading to genome reprogramming from a resting to activated state (Hawiger J. Innate immunity and inflammation a transcriptional paradigm. Immunologic research.2001, 23(2-3) 99-109. Epub 2001/07/11. doi: 10.1385/IR:23:2-3:099. PubMed PMID: 11444396.). A plethora of genes that encode inflammatory cytokines and chemokines, signal transducers (cyclooxygenase, nitric oxide synthase), and cell adhesion molecules are activated. This "genomic storm" raises blood levels of cytokines and chemokines and mobilizes expression of other mediators (Xiao W, Mindrinos M N. Seok J. Cuschieri J, Cuenca A G, Gao H, Hayden D L, Hennessy L, et al. A genomic storm in critically injured humans. The Journal of experimental medicine. 2011; 208(13):2581-90. Epub 2011/11/24. doi: 10.1084/jem.20111354. PubMed PMID:

22110166, PubMed Central PMCID: PMC3244029). Importin β can also bind and transport some TFs independently, without forming dimers with importins α (Lee S J, Sekimoto T. Yamashita E, Nagoshi E, Nakagawa A, Imamoto N, Yoshimura M, Sakai H, et al. The structure of importin-beta bound to SREBP-2: nuclear import of a transcription factor. Science.2003; 302(5650): 1571-5. Epub 2003/12/03 doi: 10.1126/science.1088372. PubMed PMID: 14645851.) Sterol Response Element-Binding Proteins (SREBPs), the master regulators of cholesterol, triglyceride, and fatty acid homeostasis, lack a classic NLS. Sterol deprivation sensed by their "rheostat" SREBP cleavage activating protein (SCAP) induces cells to cleave SREBPs, releasing an amino-terminal domain (nSREBP) that is translocated to the nucleus by association of the basic-helix-loop-helix leucine zipper (bHLH-Zip) region homodimer with importin β (Lee S J. Sekimoto T, Vamashita E, Nagoshi E, Nakagawa A, Imamoto N, Yoshimura M, Sakai H, et al. The structure of importin-beta bound to SREBP-2 nuclear import of a transcription factor. Science 2003; 302(5650):1571-5 Epub 2003/12/03. doi: 10.1126/science 1088372. PubMed PMID: 14645851; Horton J D, Goldstein J L, Brown M S. SREBPs: activators of the complete program of cholesterol and fatty acid synthesis in the liver. The Journal of clinical investigation. 2002; 109(9): 1125-31. Epub 2002/05/08. doi: 10.1172/JC115593. PubMed PMID: 11994399. PubMed Central PMCID: PMC 150968).

Many inflammatory diseases are not adequately treated using conventional therapeutics. Steroidal anti-inflammatory drugs (e.g., hydrocortisone, prednisone, and methylprednisolone) have significant side effects increasing blood glucose, blood lipids and body fat distribution, skin thinning and delayed wound healing, muscle weakness, increased susceptibility to infections, cataract, increased in eye pressure, stomach ulcers, and psychiatric disturbances. Non-steroidal anti-inflammatory drugs (e.g., aspirin, ibuprofen, naproxen, celebrex) may cause fluid retention leading to edema, kidney failure (primarily with chronic use), liver failure, ulcers and prolonged bleeding after an injury or surgery. Accordingly, anti-inflammatory therapeutics that are effective and that do not cause such side effects are greatly needed.

BRIEF SUMMARY

The present invention relates to compositions, methods, and kits for treating diseases mediated by inflammation (e.g., autoimmune, microbial, and metabolic, diseases), as well as inflammation-based neoplastic and posttraumatic diseases that afflict millions of people in the United States and globally. They suffer psoriasis, lupus, rheumatoid arthritis, diabetes, coronary heart disease, bronchitis, asthma, hepatitis, and kidney disease, among others. By modulating nuclear transport mediated by nuclear import shuttles, importins/karyopherins alpha and beta, the inflammatory basis of these diseases can be suppressed. The compositions include at least one importin beta-selective nuclear transport modifier (NTM) and/or at least one importin alpha-selective NTM, and/or at least one importin alpha-specific NTM, and/or at least one inhibitor of importin alpha and importin beta complex formation (i.e., an inhibitor of an importin alpha and importin beta interaction). Importin beta-selective and importin alpha-selective NTMs can be, for example, cell-penetrating peptides, peptide mimetics, nucleic acids (e.g., microRNA, anti-microRNA) or small molecules. The experiments described herein identify importins alpha and importins beta as "druggable" targets for a new class of cell-penetrating NTMs. For example, newly-designed peptides selective for importins alpha and beta are tested in cell-based assays and in preclinical models of inflammatory diseases. The compositions, methods, and kits described herein provide several advantages. For example, widely used steroidal anti-inflammatory drugs (e.g., hydrocortisone, prednisone, and methylprednisolone) have significant side effects increasing blood glucose, blood lipids and body fat distribution, skin thinning and delayed wound healing, muscle weakness, increased susceptibility to infections, cataract, increased in eye pressure, stomach ulcers, and psychiatric disturbances. The compositions, methods, and kits described herein provide for treatments that are free of some of these side effects in preclinical models. As another widely used example, non-steroidal anti-inflammatory drugs (e.g., aspirin, ibuprofen, naproxen, celebrex) may cause fluid retention leading to edema, kidney failure (primarily with chronic use), liver failure, ulcers and prolonged bleeding after an injury or surgery. The compositions, methods, and kits described herein provide for treatments that are free of some of these side effects in preclinical models.

Nuclear Transport Modifiers include but are not limited to SEQ ID NOs: 1-6, 9-30. Any cell-penetrating peptide or peptidomimetic, or small molecule that is capable of modulating a nuclear transport adaptor and changing its ability to facilitate or enable entry of a transcription factor into the nucleus may be a Nuclear Transport Modifier.

Unless otherwise defined, all technical terms used herein have the same meaning as commonly understood by one of ordinary skill in the art to which this invention belongs.

As used herein, the terms "Nuclear Transport Modifier" and "NTM" mean a compound, small molecule, peptide, or nucleic acid that is capable of modulating (e.g., decreasing the activity or expression of) at least one nuclear transport adaptor (e.g., importin alpha, importin beta) and thus reducing the transport of factors, such as transcription factors and other karyophilic proteins, into the nucleus. These terms are used interchangeably with "inhibitor of nuclear import" and "nuclear import inhibitor."

By the phrases "importin beta-selective Nuclear Transport Modifier (NTM)" and "importin beta-selective NTM" is meant any NTM that binds to importin beta 1 and modifies its nuclear transport function while sparing a similar function of importins alpha and that modulates nuclear transport of at least one intracellular protein, e.g., an intracellular protein that regulates cell responses to metabolic and proinflammatory stimuli. Typically, the importin beta-selective NTM includes a peptide sequence that includes an SSHR domain derived from Signal Sequence Hydrophobic Region of Fibroblast Growth Factor 4 and a hydrophilic cargo to counterbalance hydrophobic properties of SSHR.

By the phrases "importin alpha-selective Nuclear Transport Modifier (NTM)" and "importin alpha-selective NTM" is meant any NTM that binds to major and/or minor binding pockets of one or more of importins alpha that recognize their own autoinhibitory regions or other proteins that bear a nuclear localization sequence (NLS) and are larger than approximately 45 kD (e.g., proinflammatory stress-responsive transcription factors) and that modulate nuclear transport of at least one intracellular protein, e.g., an intracellular protein that regulates cell responses to proinflammatory and metabolic stimuli. Typically, the importin alpha-selective NTM is the sequence of or a sequence derived from AAVALLPAVXLAXXAPCVQRKRQKLMPC (SEQ ID NO: 1), where X represents any amino acid from the group of hydrophobic or special amino acids (e.g., cysteine, glycine, and proline, non-natural amino acids) (e.g., cMN50.1 peptide).

As used herein, the phrases "nuclear import adaptor" and "nuclear transport adaptor" mean a cell component capable of mediating transport of a protein usually larger than 45 kD (e.g., a transcription factor) into the nucleus. An example of a nuclear transport adaptor is an importin also known as a karyopherin. Examples of importin alpha include importin alpha 1, importin alpha 3, importin alpha 4, importin alpha 5, importin alpha 6, and importin alpha 7. An example of importin beta includes importin beta 1 (KPNB1) and several importin beta-like proteins such as importin beta 2, transportin and others).

By the term "cargo" is meant a peptide fragment that comprises functionally active sequence designed to modulate nuclear transport function of importins alpha and/or beta. In Table 1, "Cargo" refers to sequences of functionally active hydrophilic motifs (fragments) listed as linear or cyclized through addition of cysteine at the amino- and carboxy-termini of respective linear peptides Both linear and cyclized sequences are fused to a hydrophobic membrane translocation motif denoted SSHR.

When referring to cargo, the terms "specific" and "selective" can be used interchangeably. In general, "specific" typically refers to a sequence specific for a given importin alpha. Alternatively, when cargo is not able to bind a specific importin alpha, the resulting NTM is specific for importin beta. If an NTM binds both importin beta and importin alpha 5, then it is "bi-specific." If importin beta binding function is lost, then an NTM is selective for importin alpha.

As used herein, "protein" and "polypeptide" are used synonymously to mean any peptide-linked chain of amino acids, regardless of length or post-translational modification, e.g., glycosylation or phosphorylation.

By the term "gene" is meant a nucleic acid molecule that codes for a particular protein, or in certain cases, a functional or structural RNA molecule.

As used herein, a "nucleic acid" or a "nucleic acid molecule" means a chain of two or more nucleotides such as RNA (ribonucleic acid) and DNA (deoxyribonucleic acid).

The terms "patient," "subject" and "individual" arc used interchangeably herein, and mean a subject (e.g., vertebrate, mammalian (such as human), reptilian, piscine, avian, etc.) to be treated, diagnosed and/or to obtain a biological sample from.

As used herein, "bind," "binds," or "interacts with" means that one molecule recognizes and adheres to a particular second molecule in a sample or organism, but does not substantially recognize or adhere to other structurally unrelated molecules in the sample. Generally, a first molecule that "specifically binds" a second molecule has a binding affinity greater than about $10^8$ to $10^{12}$ moles/liter for that second molecule and involves precise "hand-in-a-glove" docking interactions that can be covalent and noncovalent (hydrogen bonding, hydrophobic, ionic, and van der Waals).

The term "labeled," with regard to a peptide, small molecule, nucleic acid, protein, probe or antibody, is intended to encompass direct labeling of the peptide, small molecule, nucleic acid, protein, probe or antibody by coupling (i.e., physically or chemically linking) a detectable substance (detectable agent) to the peptide, small molecule, nucleic acid, protein, probe or antibody.

As used herein, the terms "therapeutic," and "therapeutic agent" are used interchangeably, and are meant to encompass any molecule, chemical entity, composition, drug, therapeutic agent, chemotherapeutic agent, or biological agent capable of preventing, ameliorating, or treating a disease or other medical condition. The term includes small molecule compounds, antisense reagents, siRNA reagents, anti-microRNAs (antagomiRs) antibodies, enzymes, peptides organic or inorganic molecules, cells, natural or synthetic compounds and the like.

As used herein, the term "treatment" is defined as the application or administration of a therapeutic agent to a patient or subject, or application or administration of the therapeutic agent to an isolated tissue or cell line from a patient or subject, who has a disease, a symptom of disease or a predisposition toward a disease, with the purpose to cure, heal, alleviate, relieve, alter, remedy, ameliorate, improve or affect the disease, the symptoms of disease, or the predisposition toward disease.

Accordingly, described herein is a composition for treating an inflammatory disease or disorder (e.g., autoimmune, microbial, metabolic, neoplastic, and posttraumatic disease) in a subject. The composition includes a pharmaceutically acceptable carrier and at least one (e.g. one, two, three, etc.) importin beta-selective NTM including an SSHR domain and a cargo that does not bind to any importin alpha, or at least one (e.g., one, two, three, etc.) importin alpha-selective NTM, in an amount effective for modifying entry of at least one (e.g., one, two, three, etc.) transcription factor (e.g., NFκB, AP-1, NFAT, STAT1, SREBP1a, SREBP1c, and SREBP2, and ChREBP) into a cell's (e.g., a mammalian cell's) nucleus and for treating the inflammatory disease or disorder. The at least one importin alpha-selective NTM is a peptide or compound that binds to one or more binding pockets of an importin alpha and that modulates nuclear transport of at least one intracellular protein. Modifying entry of at least one transcription factor into a cell's nucleus includes inhibiting entry of the at least one transcription factor into the cell's nucleus. The at least one importin beta-selective NTM can have an amino acid sequence from the group of: SEQ ID NOs: 2 and 6 (e.g., AAVALLPAVLLALLAPVQRDEQKLMP (SEQ ID NO: 6). The at least one importin alpha-selective NTM can have, for example, the amino acid sequence AAVALLPAVXLAXXAPCVQRKRQKLMPC (SEQ ID NO:1). The composition can be administered with a corticosteroid or a non-steroidal anti-inflammatory agent. In another embodiment, the composition can further include a corticosteroid or a non-steroidal anti-inflammatory agent. The non-steroidal anti-inflammatory agent can be, for example, acetaminophen or ibuprofen.

Also described herein is a method of treating or preventing inflammation in a mammalian subject (e.g., a human subject having an autoimmune, metabolic, microbial, posttraumatic or neoplastic disease). The method includes administering a composition including a pharmaceutically acceptable carrier and at least one importin beta-selective NTM including an SSHR domain and a cargo to the mammalian subject in an amount effective for modifying entry of at least one transcription factor (e.g., NFκB, AP-1, NFAT, STAT1, SREBP1a, SREBP1c, and SREBP2, and ChREBP) into a cell's nucleus and for treating or preventing inflammation in the mammalian subject. In the method, the at least one importin beta-selective NTM binds to and inhibits the activity of at least one importin beta. Modifying entry of at least one transcription factor into a cell's nucleus includes inhibiting entry of the at least one transcription factor into the cell's nucleus Administration of the composition generally results in inhibition of at least one signaling pathway associated with the inflammation. The at least one importin beta-selective NTM can have an amino acid sequence from the group of SEQ ID NOs: 2 and 6 (e.g., the amino acid sequence AAVALLPAVLLALLAPVQRDEQKLMP (SEQ ID NO: 6). The composition can be administered by any suitable route, e.g., orally or subcutaneously.

Further described herein is a method of treating or preventing inflammation in a mammalian subject. The method includes administering a composition including a pharmaceutically acceptable carrier and at least one importin alpha-selective NTM to the mammalian subject in an amount effective for modifying entry of at least one transcription factor into a cell's nucleus and for treating or preventing inflammation in the mammalian subject. The at least one important alpha-selective NTM is a peptide or compound that binds to one or more binding pockets of an importin alpha and that modulates nuclear transport of at least one intracellular protein. The at least one importin alpha-selective NTM can be an importin alpha 5-specific NTM and an importin alpha 7-specific NTM. The at least one importin alpha-selective NTM can have the amino acid sequence AAVALLPAVXLAXXAPCVQRKRQKLMPC (SEQ ID NO: 1). The at least one importin alpha-selective NTM binds to and inhibits the activity of the at least one importin alpha. Modifying entry of at least one transcription factor into a cell's nucleus includes inhibiting entry of the at least one transcription factor into the cell's nucleus. The at least one importin alpha-selective NTM can be specific for importin alpha 5, for example. In some embodiments, the at least one importin alpha-selective NTM includes an Importin Alpha Diversity Region 1 or 2 sequence. The composition can be administered with a corticosteroid or a non-steroidal anti-inflammatory agent. In another embodiment, the composition can further include a corticosteroid or a non-steroidal anti-inflammatory agent. The non-steroidal anti-inflammatory agent can be, for example, acetaminophen or ibuprofen.

Yet further described herein is a method of treating or preventing inflammation in a mammalian subject. The method includes administering a composition including a pharmaceutically acceptable carrier and at least one agent that inhibits an interaction between at least one importin alpha (e.g., importin alpha 1, importin alpha 3, importin alpha 4, importin alpha 5 and importin alpha 7), and at least one importin beta and that modulates nuclear transport of at least one intracellular protein, to the mammalian subject in an amount effective for modifying entry of at least one transcription factor into a cell's nucleus and for treating or preventing inflammation in the mammalian subject. Typically, the at least one agent binds specifically to the at least one importin alpha and is an importin alpha-selective inhibitor.

Additionally described herein is a kit for treating or preventing inflammation in a mammalian subject. The kit includes a composition including a pharmaceutically acceptable carrier and a therapeutically effective amount of at least one (e.g., one, two, three, etc.) importin beta-selective NTM and/or at least one (e.g., one, two, three, etc.) importin alpha-selective NTM, and/or at least one (e.g., one, two, three, etc.) importin alpha-specific NTM, and/or at least one (e.g., one, two, three, etc.) inhibitor of importin alpha and importin beta complex formation, in a therapeutically effective amount. This amount is typically an amount effective for decreasing one or more of: blood levels of proinflammatory cytokines and chemokines, C-reactive protein, lipids, and liver transaminases, and decreasing or abrogating inflammation in the subject. The kit also includes packaging and instructions for use.

Also encompassed by the invention is a method of treatment for wound healing. In such a method, a composition described herein can be administered topically to a subject in need thereof. For all of the compositions described herein, any suitable route of administration can be used. For example, oral administration with a chewable polymeric vehicle is encompassed by the invention. As another example, subcutaneous administration of degradable polymers with controlled release of an NTM or composition including an NTM as described herein is encompassed by the invention and may find particular use in methods of treating inflammation-mediated diseases.

Although compositions, kits, and methods similar or equivalent to those described herein can be used in the practice or testing of the present invention, suitable compositions, kits, and methods are described below. All publications, patent applications, and patents mentioned herein are incorporated by reference in their entirety. In the case of conflict, the present specification, including definitions, will control. The particular embodiments discussed below are illustrative only and not intended to be limiting.

DETAILED DESCRIPTION

Described herein are compositions and methods for treating diseases mediated by inflammation, including autoimmune, metabolic, microbial, neoplastic, and postraumatic diseases. The compositions include one or more importin beta-selective or importin alpha-selective NTMs. Interaction of the NTM hydrophilic module, N50 peptide, derived from the NLS of NFκB1/p50, with endogenous human importins/karyopherins alpha, was analyzed to determine the mechanism of NTM modulation of importin alpha-mediated nuclear transport. It was shown that N50 peptide forms stable complexes with multiple importins/karyopherins alpha. However, only interaction with importin alpha 5 (Imp α5) displayed specific, high-affinity binding. The 2:1 stoichiometry of the N50-Imp α5 interaction (KD1=73 nM, KD2=140 nM) indicated occupancy of both major and minor NLS binding pockets Utilizing in silico 3-dimensional docking models and comparative structural analysis, a structural component of the Imp α5 major NLS binding pocket was identified that may stabilize N50 binding. Imp α5 also displayed rapid stimulus-induced turnover, which could influence its availability for nuclear transport during the inflammatory response. These results provide direct evidence that N50 peptide selectively targets Imp α5, encouraging use of NLS-derived peptides as new tools to modulate inflammatory disorders.

In the Examples section, the following are described in more detail: identification of importin alpha 5/karyopherins alpha 1 as a target for anti-inflammatory action of cell-penetrating peptides or their mimetics, identification of importins alpha-specific peptides based on autoinhibitory regions of importins alpha, identification of different intracellular lifespans of importins alpha and a method of their extension; identification of importins alpha diversity regions for their use as a platform for design of peptides and peptide mimetics to modulate nuclear transport of importins alpha, and design, synthesis and testing of an importin beta-selective NTM.

As described below, we designed and developed an importin beta-selective NTM termed cSM12 that spares importin alpha 5-mediated import (i.e., this peptide allows importins alpha-mediated transport to proceed). Its sequence (SEQ ID NO: 2) is:

A-A-V-A-L-L-P-A-V-L-L-A-L-L-A-P-C-V-Q-R-D-E-Q-K-L-M-P-C

Figure 10:
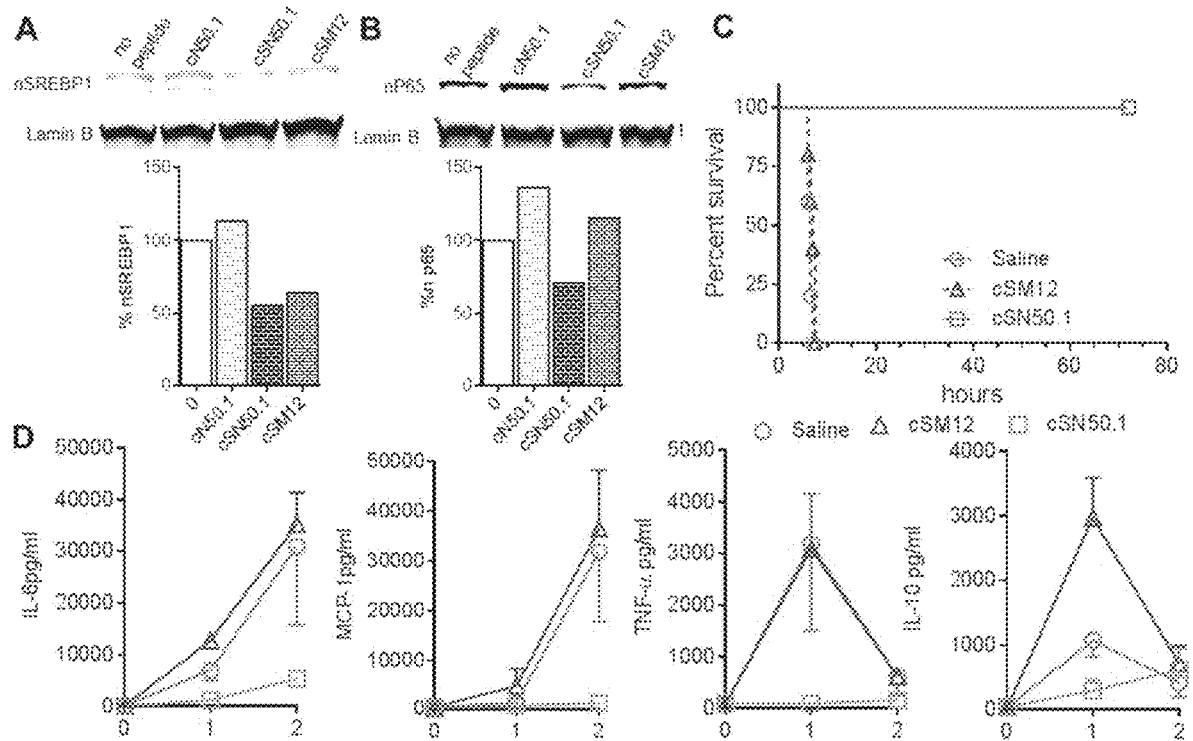
FIG. 10 shows that an importin β-specific NTM, cSM12, inhibits nuclear translocation of SREBPs, but not NF-κB RelA (p65), while bispecific cSN50.1 peptide inhibits nuclear translocation of both RelA and SREBP1. This difference in specificity is also reflected by differential effect on survival and cytokines and chemokines production in mice challenged with LPS, the most potent biologic inducer of inflammation A. SREBP1 immunoblot analysis of nuclear extracts from Hep-G2 cells depleted of lipids by treatment with hydroxy propyl-β-cyclodextrin and treated with 30 μM peptides as indicated for 2 hours B. NF-κB RelA immunoblot analysis of nuclear extracts from Hep-G2 cells treated with 30 μM peptides as indicated for 30 min then stimulated with 5 ng/ml hTNF-α for 30 min. In A and B, Lamin B=loading control for normalization C. Survival of wild-type C57BL/6 mice challenged with 1 μg LPS+20 mg D-galactosamine i.p. and treated with i.p. injections of equimolar amounts of peptides indicated, or mock-treated with saline Blood was collected at 1 h and 2 h post-LPS. D. Cytokines and chemokines in plasma from blood collected in C. Please note that 100% mice treated with bi-specific cSN50.1 peptide survived whereas all mice treated with an importin P-specific NTM died. Similarly, this peptide did not suppress elevated proinflammatory cytokines and chemokines in blood of animals challenged with LPS whereas bi-specific cSN50.1 peptide did suppress these mediators of inflammation, which are dependent on importin alpha-mediated nuclear transport of proinflammatory SRTFs.
Figure 11:
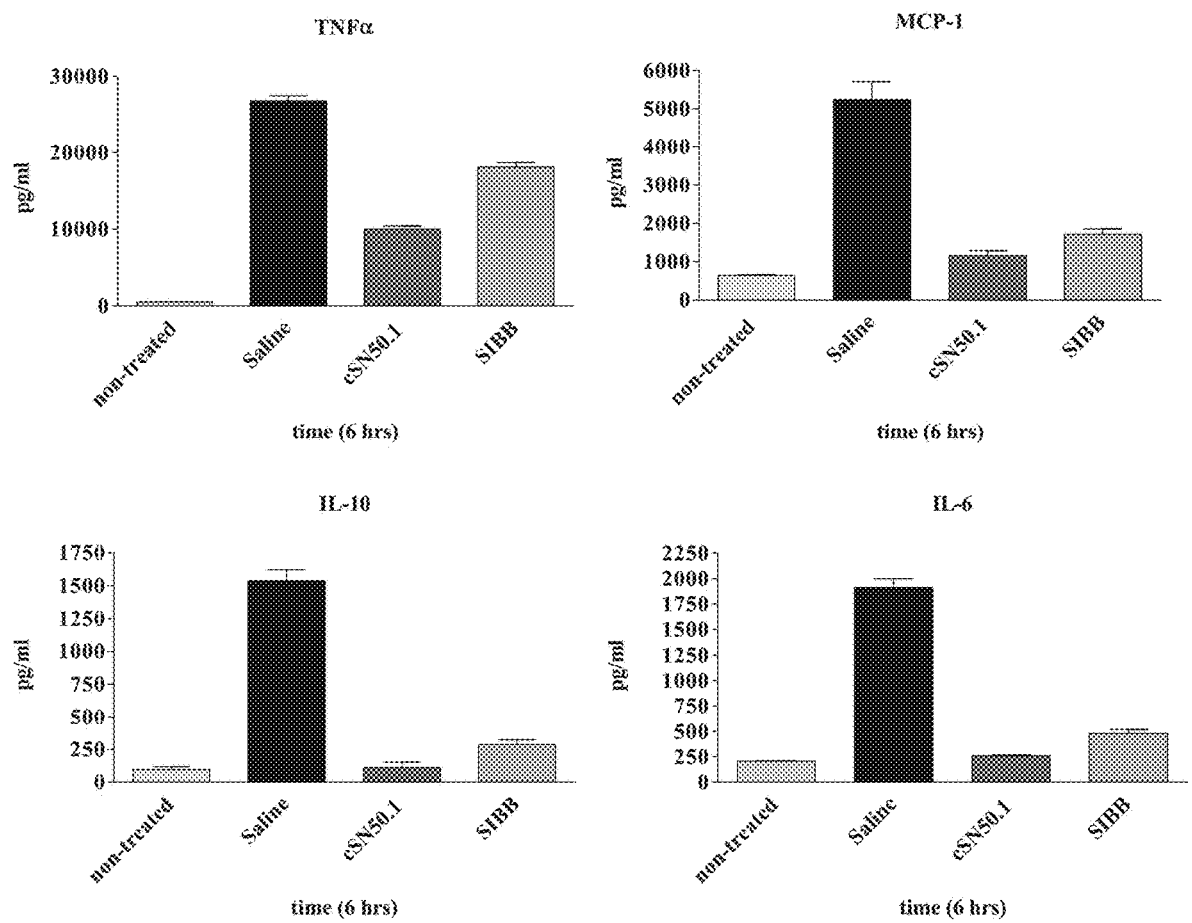
FIG. 11 shows that cell-penetrating inhibitor of importin alpha 1 interaction with importin beta termed SIBB peptide (see Table 1) inhibits production of proinflammatory cytokines and chemokine MCP-1 in mouse macrophage cell line. RAW264.7 cells ($5 \times 10^5$ per well) were treated with saline (6 μL, black), 30 μM cSN50.1 (red) or 30 μM SIBB (green) 30 min prior LPS stimulation (2 ng/ml). Cells were incubated at 37° C. for 6 hours and supernatants were collected for CBA cytokines/chemokine analysis.
Figure 12:
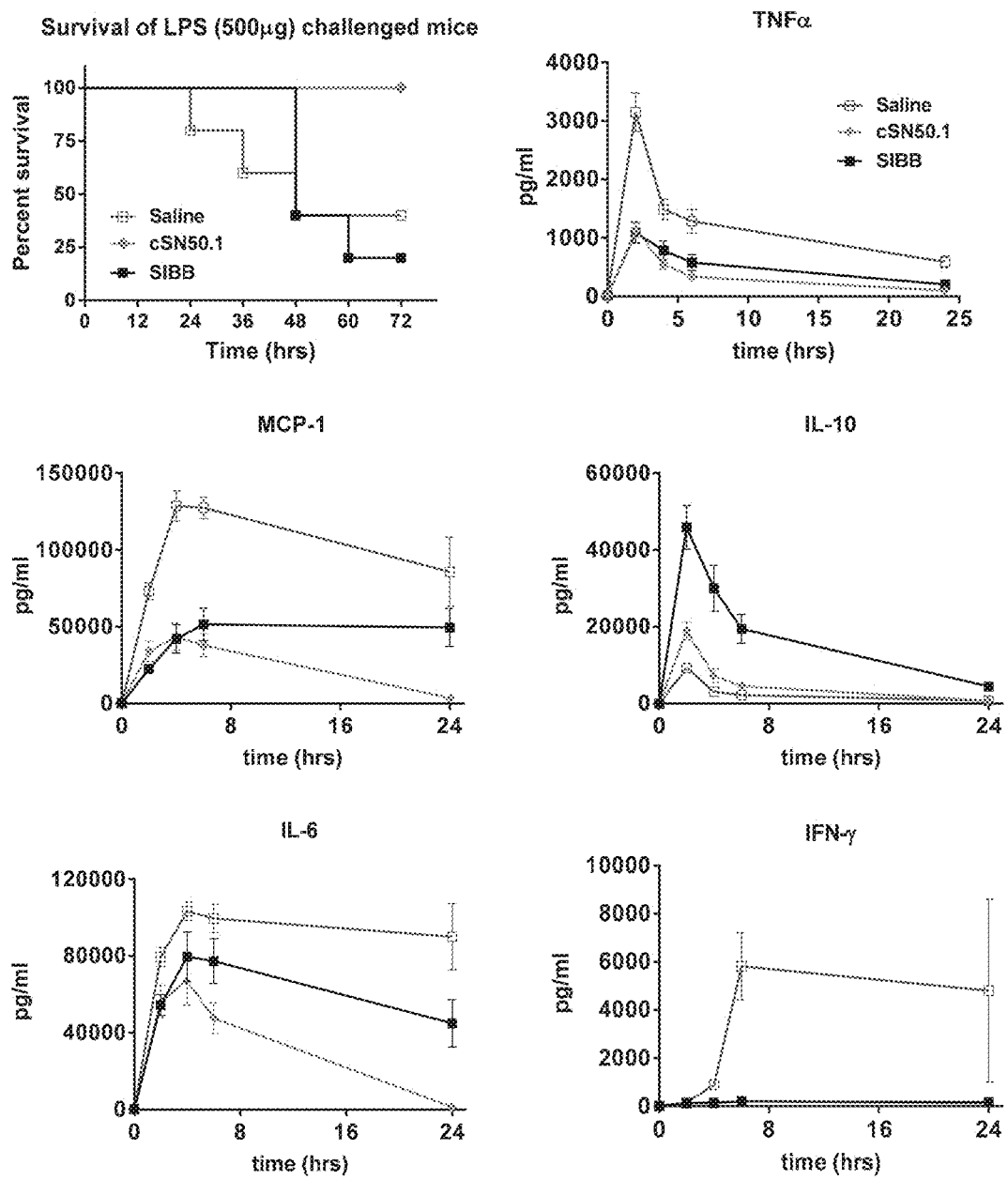
FIG. 12 shows that inhibitor of importin alpha 1 interaction with importin beta termed SIBB peptide (see Table 1) did not improve survival of mice challenged with LPS whereas it displayed suppression of cytokines in blood. These results indicate that SIBB peptide is active in cultured macrophage cells and in vivo but not sufficiently potent to protect mice from lethal shock In comparison, a bi-specific cSN50.1 peptide that binds to importin alpha 5 and importin beta is fully protective in LPS-induced systemic inflammation C57Bl/6 mice (10 week old, female), challenged with 500 μg LPS were treated with saline/vehicle (8×200 μL, open blue squares), 8×0.7 mg of cSN50.1 (solid red diamond) or 8×0.8 mg of SIBB (solid black squares) according to following treatment protocol: −30 min, +30 min, 1.5 h, +3.5 h. +6 h, +12 h and +24 h post LPS challenge. Blood samples were collected at 2, 4, 6 and 24 hours after LPS and CBA analysis of cytokines/chemokine was performed.

Referring to FIG. 10, the cSM12 peptide that is selective for importin beta does not modulate proinflammatory signaling pathways induced by proinflammatory agonist lipopolysaccharide (LPS) and mediated by importin alpha as LPS-challenged mice were not protected from lethal endotoxic shock and plasma levels of proinflammatory cytokines and chemokines were not suppressed by cCM12, while bi-specific cSN50. 1 was protective against both (FIGS. 10C and D). The control peptide cN50.1, which does not contain an SSHR motif and does not enter cells, has no effect on either pathway. In other words, this importin beta-selective peptide (cSM12) modifies nuclear transport of lipid-regulating Sterol Regulatory Element Binding Proteins (SRFBP 1 and 2) (FIG. 10A) but does not change the nuclear import of proinflammatory Stress-Responsive Transcription Factors (SRTFs) such as NFκB (see nP65 in FIG. 10B) Therefore, cCM12 peptide is not protecting mice from death in a preclinical model of systemic inflammation induced by LPS whereas cSN50.1 peptide is (see FIG. 10C). Concomitantly, proinflammatory cytokines and chemokines are not suppressed by cCM12 peptide in contrast to cSN50.1 peptide. Thus, the cCM12 peptide represents a new-class of importin beta-selective NTMs.

Figure 9:
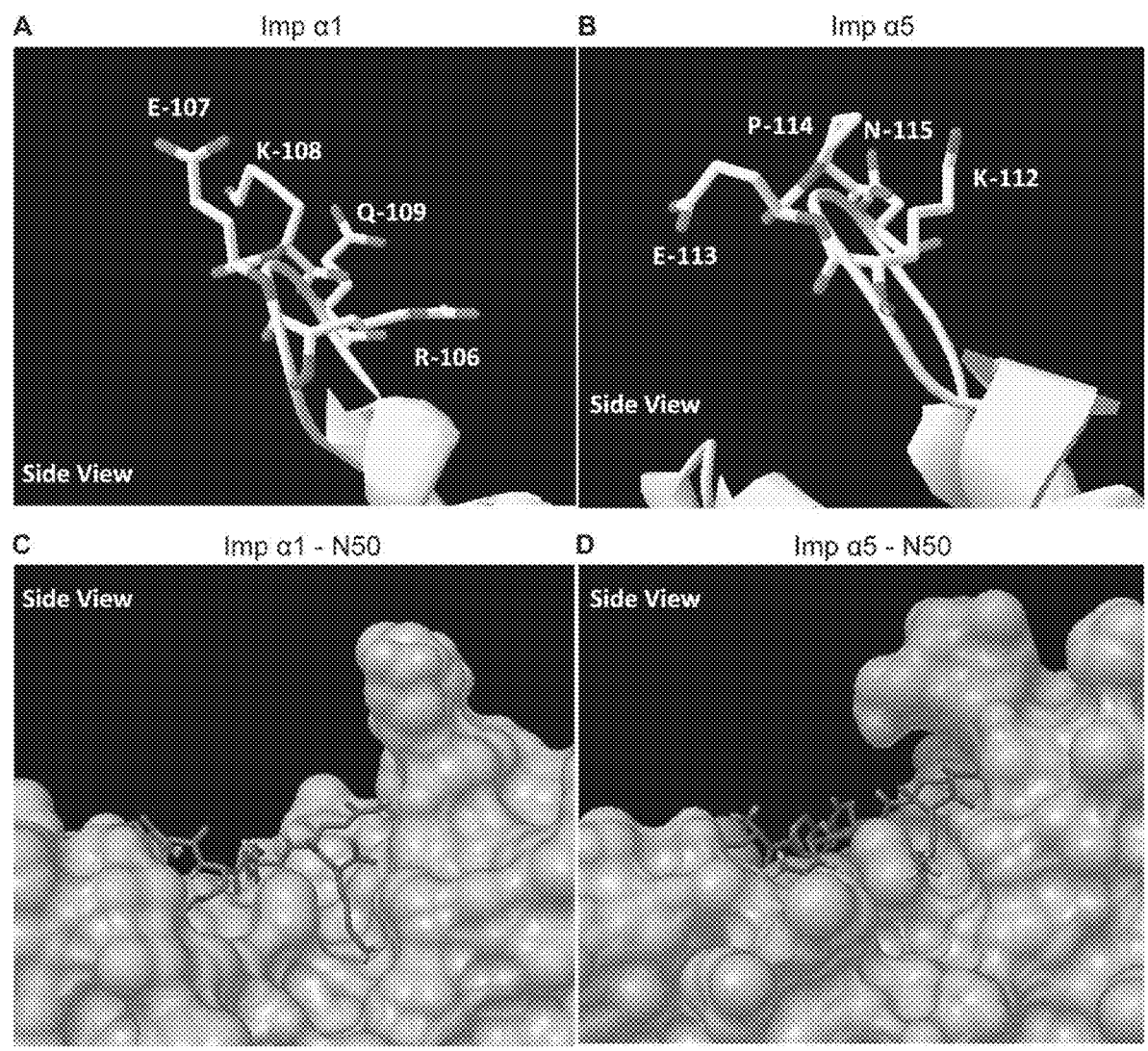
FIG. 9 shows the composition of loop A in Imp α1 and α5 and its differential effect on docking of N50 to the major NLS binding pocket A and B, Ribbon structure and composition of loop A of A, human Imp α1 (KPNA2), and B, human Imp α5 (KPNA1). Structures were visualized in DeepView. C and D, 3-D models of p50 NLS docking to the molecular surface of C, human Imp α1 (KPNA2), and D, human Imp α5 (KPNA1). Please note that loop A may provide stability to the p50 NLS-Imp α5 complex while no such role is apparent for loop A in Imp α1. Docking models were generated by AutoDock Vina 1.1.2 and visualized by PythonMoleculeViewer 1.5.6. Panel A discloses "R-106, E-107, K-108, Q-109" as residues 106-109 of SEQ ID NO: 41 and Panel B discloses "K-112, E-113, P-114, N-115" as residues 112-115 of SEQ ID NO: 44.

NTMs target nuclear transport adaptors. NTMs modulate signaling to the nucleus mediated by transcription factors that include but are not limited to NFκB, AP-1, NFAT, STAT1 that utilize importins alpha and beta heterodimer, SREBP1a, SREBP1c, and SREBP2, that utilize solely importin beta for nuclear transport (as presented in FIG. 9 in Liu Y et al., JAHA 2013 and in FIGS. 4A and 4B of U.S. patent application Ser. No. 14/349,918 which is incorporated herein by reference) whereas ChREBP can utilize both importins alpha and beta for nuclear translocation. SRTFs such as NFκB, AP-1, NFAT, STAT1 are transported to the nucleus in response to proinflammatory stimuli. In the nucleus, SRTFs activate genes that encode mediators of inflammation (Hawiger, J., Immunol Res 23 (2-3), 99-109 (2001)). Examples of NTMs include SN50, cSN50 and cSN50.1 described in more detail in the following paragraphs, as well as the sequences set forth in Table 1.

SN50, cSN50, and cSN50.1 are fragment linked peptides combining the signal sequence hydrophobic region (SSHR) of the fibroblast growth factor 4 (-FGF4) and the nuclear localization signal (NLS) of the p50 subunit of NFκB1. Any mimetics, derivatives, or homologs of SN50, cSN50, and cSN50.1 may be used in the compositions, methods, and kits disclosed herein. The sequence of SN50 is AAVALLPAVL-LALLAPVQRKRQKLMP (SEQ ID NO: 3). Generation and use of SN50 is described in U.S. Pat. No. 7,553,929.

cSN50 is a cyclized peptide combining the hydrophobic domain of the K-FGF signal sequence with the NLS of the p50 subunit of NFκB1 and inserting a cysteine on each side of the NLS to form an intrachain disulfide bond. The amino acid sequence of cSN50 is AAVALLPAVLLAL-LAPCYVQRKRQKLMPC (SEQ ID NO: 4). Any mimetics, derivatives, or homologs of cSN50 may be used in the compositions, methods, and kits disclosed herein.

cSN50.1 is a cyclized peptide having the sequence of cSN50 with the exception that the tyrosine at position 18 of cSN50, adjacent to the first cysteine, has been removed. Methods of making and using cSN50 are described, for example, in U.S. Pat. Nos. 7,553,929 and 6,495,518. The amino acid sequence of cSN50.1 is AAVALLPAVLLAL-LAPCVQRKRQKLMPC (SEQ ID NO: 5). The tyrosine at position 18 was removed from the sequence of cSN50 to increase solubility. cSN50 is soluble at levels of ranging from 2.0 mg/mL to 40 mg/mL depending on the method of synthesis and purification whereas cSN50.1 is soluble at levels of at least 100 mg/ml. Any mimetics, derivatives, or homologs of cSN50.1 may be used in the compositions, methods, and kits disclosed herein. cCM12 is a cyclized peptide having the sequence of cSN50.1 with the exception that the lysine at the position 21 has been replaced by aspartic acid and the arginine residue at the position of 22 has been replaced by glutamic acid. The amino acid sequence of cCM12 is AAVALLPAVLLALLAPCVQRD-EQKLMPC (SEQ ID NO: 2).

Biological and Chemical Methods

Methods involving conventional molecular biology techniques are described herein Such techniques are generally known in the art and are described in detail in methodology treatises such as Sambrook et al. ed., (2001) Molecular Cloning: A Laboratory Manual, 3rd ed., vol. 1-3, Cold Spring Harbor Laboratory Press, Cold Spring Harbor, N.Y.; and Ausubel et al. ed., (1992) (with periodic updates) Current Protocols in Molecular Biology, ed., Greene Publishing and Wiley-Interscience, New York.

Compositions for Treating Diseases and Disorders Associated with Inflammation in a Subject Compositions (e.g., pharmaceutical compositions) described herein for treating diseases associated with inflammation include a pharmaceutically acceptable carrier and at least one importin beta-selective and/or at least one importin alpha-selective NTM in an amount effective for modifying (e.g., decreasing) entry into the nucleus of at least one transcription factor that includes but is not limited to NFκB, AP-1, NFAT, STAT1, SREBP1a, SREBP1c, and SREBP2, and ChREBP that utilize importins alpha and/or beta for nuclear transport, and treating or preventing the disease. For example, entry of at least one SREBP into the nucleus is reduced. As mentioned above, NTMs modulate signaling to the nucleus mediated by transcription factors that include but are not limited to NFκB, AP-1, NFAT, STAT1 that utilize importins alpha and beta heterodimer, SREBP1a, SREBP1c, and SREBP2, that utilize solely importin beta for nuclear transport whereas ChREBP can utilize both importins alpha and beta for nuclear translocation. In this example, the importin beta-selective NTM reduces nuclear translocation of the nuclear forms of SREBP1a, SREBP1c, and SREBP2. Any suitable importin beta-selective NTM may be used. Examples of importin beta-selective NTMs include but are not limited to peptide sequences that include an SSHR domain listed in Table 1 below and a cargo listed in Table 1 below. One example of such an importin beta-selective NTM is AAVALLPAVL-LALLAPVQRDEQKLMP (SEQ ID NO: 6) (i.e., a peptide sequence having the SSHR domain of AAVALLPAVLLAL-LAP (SEQ ID NO: 7) and the cargo of VQRDEQKLMP (SEQ ID NO: 8) as listed in Table 1 below). Additional examples of peptides designed to inhibit interaction of importin alpha with importin beta necessary for the formation of their heterodimer include AAVALLPAVLLALL-APRRRRIEVNVELRKAKK (SEQ ID NO: 9) (referred to as SIBB in Table 1), AAVALLPAVLLALLAPRRRRIEVN-VELRKAKKDD (SEQ ID NO: 10) (referred to as SI-1 in Table 1). AAVALLPAVLLALLAPRRQR-NEVVVELRKNKRDE (SEQ ID NO: 11) (referred to as SI-3 in Table 1), AAVALLPAVLLALLAPRRHR-NEVTVELRKNKRDE (SEQ ID NO: 12) (referred to as SI-4 in Table 1), AAVALLPAVLLALLAPRRR-REEEGLQLRKQKREE (SEQ ID NO: 13) (referred to as SI-5 in Table 1), AAVALLPAVLLALLAPRRR-REEEGIQLRKQKREQ (SEQ ID NO: 14) (referred to as SI-7 in Table 1) and AAVALLPAVLLALLAPCTEMRRR-RIEVC (SEQ ID NO: 15) (referred to as cSIB in Table 1). The examples of peptides designed to be specific inhibitors of imponins alpha include AAVALLPAVLLAL-LAPVELRKAKKDDQMLKRRNVSSF (SEQ ID NO: 16) (referred to as SAR1 in Table 1), AAVALLPAVLLAL-LAPVELRKNKRDEHLLKRRNVPHE (SEQ ID NO: 17) (referred to as SAR3 in Table 1), AAVALLPAVLLAL-LAPVELRKNKRDEHLLKKRNVPQE (SEQ ID NO: 18) (referred to as SAR4 in Table 1), AAVALLPAVLLAL-LAPLQLRKQKREEQLFKRRNVATA (SEQ ID NO: 19) (referred to as SAR5 in Table 1), AAVALLPAVLLAL-LAPIQLRKQKREQQLFKRRNVELI (SEQ ID NO: 20) (referred to as SAR7 in Table 1), AAVALLPAVLLAL-LAPCVELRKAKKDDQC (SEQ ID NO: 21) (referred to as cSAR1-C in Table 1), AAVALLPAVLLAL-LAPCVELRKNKRDEHC (SEQ ID NO: 22) (referred to as cSAR3-C in Table 1), AAVALLPAVLLAL-LAPCLQLRKQKREEQC (SEQ ID NO: 23) (referred to as cSAR5-C in Table 1), AAVALLPAVLLALLAPC1QLRKQKREQQC (SEQ ID NO: 24) (referred to as CSAR7-C in Table 1), AAVALL-PAVLLALLAPCQMLKRRNVSSFC (SEQ ID NO. 25) (referred to as cSAR1-N in Table 1), AAVALLPAVLLAL-LAPCHLLKRRNVPHEC (SEQ ID NO: 26) (referred to as cSAR3-N in Table 1), AAVALLPAVLLAL-LAPCHLLKKRRNVPQEC (SEQ ID NO: 27) (referred to as cSAR4-N in Table 1), AAVALLPAVLLAL-LAPCQLFKRRNVATAC (SEQ ID NO: 28) (referred to as CSAR5-N in Table 1), and AAVALLPAVLLAL-LAPCQLFKRRNVELIC (SEQ ID NO: 29) (referred to as cSAR7-N in Table 1). It is to be understood that any derivatives and/or analogues of these sequences are encompassed by the invention.

In one embodiment, an NTM as described herein has the sequence AAVALLPAVXLAXXAPVELRKNKRDE-HLLKRRNVPHE (SEQ ID NO: 30). Additional NTMs include SEQ ID NOs: 1-6 and 9-29. It is to be understood that any derivatives and/or analogues of these sequences are encompassed by the invention.

An NTM as described herein may be an inhibitor of an importin alpha 3 interaction with importin beta.

The SI-3 sequence (see Table 1) is designed to block an interaction between importin alpha and importin beta. Hence, this peptide is a cell-penetrating inhibitor of an importin alpha and importin beta interaction. It is to be understood that any derivatives and/or analogues of this sequence is encompassed by the invention.

TABLE 1

Peptide sequences

|  | SSHR§ | Cargo | SEQ ID NO: | Comments |
|---|---|---|---|---|
| SM12 | AAVALLPAVLLALLAP | VQRDEQKLMP | 6 | Importin beta-selective inhibitor (binding studies) |
| SIBB | AAVALLPAVLLALLAP | RRRRIEVNVELRKAKK | 9 | inhibitor of Imp alpha 1-importin beta interaction |
| SI-1 | AAVALLPAVLLALLAP | RRRRIEVNVELRKAKKDD | 10 | Inhibitor of Imp alpha 1-importin beta interaction |
| SI-3 | AAVALLPAVLLALLAP | RRQRNEVVVELRKNKRDE | 11 | Inhibitor of Imp alpha 3-importin beta interaction |
| SI-4 | AAVALLPAVLLALLAP | RRHRNEVTVELRKNKRDE | 12 | Inhibitor of Imp alpha 4-importin beta interaction |
| SI-5 | AAVALLPAVLLALLAP | RRRREEGLQLRKQKREE | 13 | Inhibitor of Imp alpha 5-importin beta interaction |
| SI-7 | AAVALLPAVLLALLAP | RRRREEEGIQLRKQKREQ | 14 | Inhibitor of Imp alpha 7-importin beta interaction |
| SAR1 | AAVALLPAVLLALLA | VELRKAKKDDQMLKRRNVSSF | 16 | Imp alpha 1-specific |
| SAR3 | AAVALLPAVLLALLAP | VELRKNKRDEHLLKRRNVPHE | 17 | Imp alpha 3-specific |
| SAR4 | AAVALLPAVLLALLAP | VELRKNKRDEHLLKKRNVPQE | 18 | Imp alpha 4-specific |
| SAR5 | AAVALLPAVLLALLAP | LQLRKQKREEQLFKRRNVATA | 19 | Imp alpha 5-specific |
| SAR7 | AAVALLPAVLLALLAP | IQLRKQKREQQLFKRRNVELI | 20 | Imp alpha 7-specific |
| cMN50.1 | AAVALLPAVXLAXXAP | CVQRKRQKLMPC | 1 | Imp alpha 5-selective |

TABLE 1-continued

Peptide sequences

| | SSHR[§] | Cargo | SEQ ID NO: | Comments |
|---|---|---|---|---|
| cSM12 | AAVALLPAVLLALLAP | CVQRDEQKLMPC | 2 | Imp beta-selective (cell culture and preclinical studies) |
| cSIB | AAVALLPAVLLALLAP | CTEMRRRRIEVC | 15 | Inhibitor of Imp alpha 1-importin beta interaction |
| cSAR1-C | AAVALLPAVLLALLAP | CVELRKAKKDDQC | 21 | Imp alpha 1-specific Proximal to C-terminal |
| cSAR3-C | AAVALLPAVLLALLAP | CVELRKNKRDEHC | 22 | Imp alpha 3-specific Proximal to C-terminal |
| cSAR5-C | AAVALLPAVLLALLAP | CLQLRKQKREEQC | 23 | Imp alpha 5-specific Proximal to C-terminal |
| cSAR7-C | AAVALLPAVLLALLAP | CIQLRKQKREQQC | 24 | Imp alpha 7-specific Proximal to C-terminal |
| cSAR1-N | AAVALLPAVLLALLAP | CQMLKRRNVSSFC | 25 | Imp alpha 1-specific Proximal to N-terminal |
| cSAR3-N | AAVALLPAVLLALLAP | CHLLKRRNVPHEC | 26 | Imp alpha 3-specific Proximal to N-terminal |
| cSAR4-N | AAVALLPAVLLALLAP | CHLLKKRNVPQEC | 27 | Imp alpha 4-specific Proximal to N-terminal |
| cSAR5-N | AAVALLPAVLLALLAP | CQLFKRRNVATAC | 28 | Imp alpha 5-specific Proximal to N-terminal |
| cSAR7-N | AAVALLPAVLLAL | CQLFKRRNVELIC | 29 | Imp alpha 7-specific Proximal to N-terminal |

[§]Signal Sequence Hydrophobic Region (SSHR)
"Cargo" comprises sequences of functionally active hydrophilic motifs (fragments) listed as linear or cyclized peptides through addition of cysteine at the amino- and carboxy-termini of respective linear peptides. Both linear and cyclized sequences are fused to hydrophobic membrane translocation motif denoted SSHR.

Encompassed by the present invention are peptides in which any of the amino acids in the SSHR are replaced to abolish importin beta binding while sparing the membrane-translocating function of the SSHR For example, the following peptide potentially would not bind importin beta but will be selective and specific for importins alpha 5-based binding: AAVALLPAVXLAXXAPCVQRKRQKLMPC (SEQ ID NO: 1), where X represents any amino acids from the group of hydrophobic or special amino acids (e.g., cMN50.1). This sequence represents an example of an importin alpha 5-selective NTM. Any suitable importin alpha-selective NTM can be used. Typically, an importin alpha-selective NTM is a peptide, peptidomimetic or small molecule that modulates the transport function of importin alpha while not changing importin beta nuclear transport function of SSHR.

Methods of Treating or Preventing Inflammatory Disorders in a Mammalian Subject

A typical method of treating or preventing an inflammatory disorder in a mammalian subject includes administering a composition including at least one importin beta-selective NTM including an SSHR domain and a cargo, or at least one importin alpha-selective NTM including peptides listed in Table 1, to the mammalian subject in an amount effective for reducing importin alpha- and/or importin beta-mediated nuclear translocation of at least one transcription factor, and reducing inflammation in the mammalian subject. In the method, the NTM reduces importin alpha-mediated nuclear translocation of stress-responsive transcription factors (SRTFs) that respond to inflammatory stress and/or reduces importin beta-mediated nuclear translocation of transcription factors that respond to metabolic stress, e.g., SREBP transcription factors by binding to importin alpha and to importin beta, respectively. Any suitable NTM can be used, e.g., one or more of the sequences disclosed herein, i.e., SEQ ID NOs:1-6 and 9-30 and/or derivatives and/or analogues thereof. The composition may be administered via any suitable route, e.g., orally or subcutaneously. The therapeutic methods of the invention in general include administration of a therapeutically effective amount of a composition described herein to a subject (e.g., animal) in need thereof, including a mammal, particularly a human.

In one embodiment, the invention provides a method of monitoring treatment progress. The method includes the step of determining a level of diagnostic marker such as blood levels of proinflammatory cytokines and chemokines, C-reactive protein, lipids, liver transaminases, etc. (e.g., any target delineated herein modulated by a composition or agent described herein, a protein or indicator thereof, etc.) or diagnostic measurement (e.g., screen, assay) in a subject suffering from or susceptible to a disorder or symptoms thereof associated with inflammation in which the subject has been administered a therapeutic amount of a composition as described herein for treating the disease or symptoms thereof. The level of marker determined in the method can be compared to known levels of marker in either healthy normal controls or in other afflicted patients to establish the subject's disease status. In preferred embodiments, a second level of marker (e.g., blood levels of proinflammatory cytokines and chemokines, C-reactive protein, lipids, liver transaminases, etc.) in the subject is determined at a time point later than the determination of the first level, and the two levels are compared to monitor the course of disease or the efficacy of the therapy. In certain preferred embodiments, a pre-treatment level of marker in the subject is determined prior to beginning treatment according to the methods described herein; this pre-treatment level of marker can then be compared to the level of marker in the subject after the treatment commences, to determine the efficacy of the treatment.

Also described herein are diagnostic and theranostic methods useful to determine whether the subject is susceptible to the treatment methods of the invention. The term "theranostics" generally refers to therapy-specific diagnostics, which is the use of diagnostic testing to diagnose the disease, choose the correct treatment regime for that disease, and monitor the patient response to therapy. Theranostic tests can be used to predict and assess drug response in individual patients, and are designed to improve drug efficacy by selecting patients for treatments that are particularly likely to benefit from the treatments. Theranostic tests are also designed to improve drug safety by identifying patients that may suffer adverse side effects from the treatment.

Kits

Described herein arc kits for treating diseases or disorders associated with inflammation in a subject. A typical kit includes: a composition including a pharmaceutically acceptable carrier and a therapeutically effective amount of at least one importin beta-selective NTM (e.g., an importin beta-selective NTM including an SSHR domain and a cargo) and/or at least one importin alpha-selective NTM (e g., a peptide sequence including a modified SSHR sequence with inactive importin beta-binding function), and/or at least one importin alpha-specific NTM, and/or at least one inhibitor of importin alpha and importin beta complex formation, typically, in an amount effective for decreasing at least one of: blood levels of proinflammatory cytokines and chemokines, C-reactive protein, lipids, liver transaminases, etc., and decreasing or abrogating inflammation, as well as packaging, and instructions for use. Optionally, kits may also contain one or more of the following: containers which include positive controls, containers which include negative controls, photographs or images of representative examples of positive results and photographs or images of representative examples of negative results.

Administration of Pharmaceutical Compositions

The administration of a composition including at least one importin beta-selective NTM (e.g., NTM including an SSHR domain and a cargo) and/or at least one importin alpha-selective NTM (e.g., a peptide sequence including one or more peptides listed in Table 1) in an amount effective for decreasing the levels of, for example, one or more of blood levels of proinflammatory cytokines and chemokines, C-reactive protein, lipids (e.g., plasma lipids), liver transaminases, etc. may be by any suitable means that results in a concentration of the therapeutic that is effective in decreasing the levels of, for example, one or more of blood levels of proinflammatory cytokines and chemokines, C-reactive protein, lipids (e.g., plasma lipids), liver transaminases, etc. At least one importin beta-selective NTM (e.g., a peptide sequence including an SSHR domain and a cargo) and/or at least one importin alpha-selective NTM (e.g., a peptide sequence including an SSHR with a loss of importin beta-binding function) may be contained in any appropriate carrier substance, and is generally present in an amount of 1-95% by weight of the total weight of the composition. The composition may be provided in a dosage form that is suitable for local or systemic administration (e.g., parenteral, subcutaneously, intravenously, intramuscularly, or intraperitoncally). The pharmaceutical compositions may be formulated according to conventional pharmaceutical practice (see, e.g., (Gennaro, A. R. ed. (2000) Remington: The Science and Practice of Pharmacy (20th ed.), Lippincott Williams & Wilkins, Baltimore, Md.; Swarbrick, J. and Boylan, J. C. eds. (1988-1999) Encyclopedia of Pharmaceutical Technolog, Marcel Dekker, New York).

Compositions as described herein may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. In one embodiment, a composition as described herein is administered via osmotic pump. The composition may be administered orally in sublingual form or with a coating protecting the composition from gastrointestinal peptidases. The formulation and preparation of such compositions are well known to those skilled in the art of pharmaceutical formulation. Formulations can be found in Gennaro supra.

Compositions for parenteral use may be provided in unit dosage forms (e.g., in single-dose ampoules), or in vials containing several doses and in which a suitable preservative may be added. The composition may be in the form of a solution, a suspension, an emulsion, an infusion device, or a delivery device for implantation, or it may be presented as a dry powder to be reconstituted with water or another suitable vehicle before use. Apart from the active agent that treats or prevents inflammation, for example, the composition may include suitable parenterally acceptable carriers and/or excipients. The active therapeutic agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing agents.

As indicated above, the pharmaceutical compositions described herein may be in a form suitable for sterile injection. To prepare such a composition, the suitable active therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer. 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Materials for use in the preparation of microspheres and/or microcapsules are, e.g., biodegradable/bioerodible polymers such as polygalactin, poly-(isobutyl cyanoacrylate), poly(2-hydroxyethyl-L-glutamine), and poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), polydactic acid), poly (glvcolic acid) or poly(ortho esters) or combinations thereof).

Formulations for oral use include tablets containing the active ingredient(s) (e.g., at least one importin beta-selective NTM and/or at least one importin alpha-selective NTM) in a mixture with non-toxic pharmaceutically acceptable excipients. Such formulations are known to the skilled artisan Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscannellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol), and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active ingredient (e.g., drug) in a predetermined pattern (e.g., in order to achieve a controlled release formulation) or it may be adapted not to release the active ingredient until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material, such as, e.g., glyceryl monostearate or glyceryl distearate may be employed.

The solid tablet compositions may include a coating adapted to protect the composition from unwanted chemical changes, (e.g., chemical degradation prior to the release of the active therapeutic substance). The coating may be applied on the solid dosage form in a similar manner as that described in Swarbrick J. and Boylan, J. C. supra. Two or more compounds or therapeutic agents (including a NTM as described herein) for treaunent of inflammation may be mixed together in the tablet, or may be partitioned. In one example, the first active therapeutic is contained on the inside of the tablet, and the second active therapeutic is on the outside, such that a substantial portion of the second active therapeutic is released prior to the release of the first active therapeutic. Therapeutic combinations that decrease the level of inflammation, for example, are identified as useful in the compositions, methods, and kits described herein.

Formulations for oral use may also be presented as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus or a spray dry ing equipment. Compositions as described herein can also be formulated for inhalation and topical applications. Combinations are expected to be advantageously synergistic.

The therapeutic methods described herein in general include administration of a therapeutically effective amount of a composition described herein to a subject (e.g., animal) in need thereof, including a mammal, particularly a human. Such treatment will be suitably administered to subjects, particularly humans, suffering from, having, susceptible to, or at risk for inflammation. Determination of those subjects "at risk" can be made by any objective or subjective determination by a diagnostic test or opinion of a subject or health care provider.

Effective Doses

The compositions (pharmaceutical compositions) described herein are preferably administered to an animal (e.g., mammalian (such as human, ovine, bovine, canine, porcine, equine, etc.), reptilian, piscine, avian, etc.) in an effective amount, that is, an amount capable of producing a desirable result in a treated animal (e.g., decreasing inflammation). Such a therapeutically effective amount can be determined according to standard methods. Toxicity and therapeutic efficacy of the compositions utilized in methods of the invention can be determined by standard pharmaceutical procedures. As is well known in the medical and veterinary arts, dosage for any one subject depends on many factors, including the subject's size, body surface area, age, the particular composition to be administered, time and route of administration, general health, and other drugs being administered concurrently. Using an established formula for extrapolating a human equivalent dose from the animal dose through normalization to body surface area (Reagan-Shaw, S., M. Nihal, and N. Ahmad. 2008. Dose translation from animal to human studies revisited. Faseb J 22: 650-661), the effective cSN50.1 peptide dose of 0.66 mg/20 g mouse translates to a manageable human dose of 200 mg/70 kg. This is similar to a standard oral dose of ibuprofen, a non-steroidal anti-inflammatory drug.

EXAMPLES

The present invention is further illustrated by the following specific examples. The examples are provided for illustration only and should not be construed as limiting the scope of the invention in any way.

Example 1

Targeting Nuclear Import Shuttles, Importins/Karyopherins Alpha, by a Peptide Mimicking the NF kappa B1/p50 Nuclear Localization Sequence It has been reported that treatment with a cell-penetrating nuclear transport modifier (NTM), cSN50.1 peptide, reduced atherosclerosis as well as elevated plasma cholesterol, triglycerides, and glucose in a mouse model of familial hypercholesterolemia (Liu et al. J Am Mean Assoc 2013, 2:e000093). Additionally, elevated cholesterol and triglycerides in the liver were reduced, along with liver enzymes ALT and AST, markers of steatohepatitis. These signs of liver inflammation were accompanied by increased phosphorylation and nuclear translocation of nuclear factor kappa B (NFκB) that was attenuated in NTM-treated mice. This outcome was consistent with the well-established anti-inflammatory function of NTMs through modulation of importin alpha (Imp α)-mediated nuclear transport of proinflammatory stress-responsive transcription factors (SRTFs), such as NFκB, activator protein 1 (AP-1), nuclear factor of activated T cells (NFAT), and signal transducer and activator of transcription 1 (STAT1) (Torgerson et al. J Immunol 1998, 161:6084-6092: Hawiger, J., Immunol Res 2001; 23:99-109). N50-containing NTMs (SN50, cSN50 and cSN50.1) are comprised of a hydrophilic N50 motif patterned on the nuclear localization sequence (NLS) region of the NFκB1/p50 subunit (see Table 2) fused to a motif from the signal sequence hydrophobic region (SSHR) of human fibroblast growth factor 4 (Liu et al., J Am Heart Assoc. 2013; 2:e000093). The SSHR allows peptides to cross the plasma membrane by an ATP- and endosome-independent mechanism, and the N50 motif was designed to bind to importins alpha during stimulus-initiated signaling and thereby limit docking of NLS-bearing SRTFs to their adaptor proteins and reduce nuclear import of activated STRFs. The surprising correction of dyslipidemia and its sequelae (fatty liver and atherosclerosis) was attributed to a second function of NTM, namely, nuclear transport modulation of sterol regulatory element-binding proteins (SREBPs), master regulators of genes involved in synthesis of cholesterol, triglycerides, and fatty acids, which do not display an NLS. We determined that NTM accomplished this newly discovered function by interaction of its SSHR motif with importin beta (Imp β), the sole nuclear transport shuttle for SREBPs (Lee et al., Science 2003; 302:1571-1575). However, the mechanism of NTM interaction with importins/karyopherins alpha (see Table 3A for nomenclature) remained unexplained. Since multiple SRTFs modulated by NTMs display monopartite or bipartite NLSs distinct from that of NFκB1/ p50, it became apparent that recognition of NTMs by importins alpha is more complex than initially thought. Therefore, a study of the interaction of the NTM module N50 with human importins alpha in terms of their turnover, cell type-specific abundance, selectivity, and accessibility of their major NLS-binding pocket was embarked upon.

Methods

Sequence analyses of importins/karyopherins alpha: Results shown in Table 3B were determined by Align Sequences Protein BLAST (Basic Local Alignment Search Tool, National Center for Biotechnology Information). PeptideCutter software was used to search for potential protease cleavage sites (ExPASy. Bioinformatics Resource Portal), and T-Coffee software was employed to analyze the sequences of all 6 human importins alpha. T-Coffee uses the Pfam database to generate a comparison, allowing a combination of results obtained with several alignment methods. It produces a global alignment and a series of local alignments. The program then combines all these alignments into a multiple alignment. The combination of local and global alignments leads to a high degree of alignment accuracy.

Cell culture: Human T lymphocytes (Jurkat T cells), human epithelial cells adapted to grow in suspension (HeLa S3), and human endothelial cells (EA.hy926, human umbilical vein endothelial cells fused with A549, human lung adenocarcinoma epithelial cells) were obtained from the American Type Culture Collection and cultured according to their recommendations.

Whole cell lysates: Whole cell lysates were prepared in two steps using a modified hypotonic buffer containing NP-40 to obtain cytosolic fractions followed by addition of salt (0.45 M NaCl) to extract nuclear proteins.

Half-life ($t_{1/2}$) of human importins: To determine $t_{1/2}$ of endogenously expressed importins, 10 μg/mL cycloheximide (CHX) was added to JurkatT cells; 30 min later cells were either left unstimulated or stimulated with 5 nM phorbol 12-myristate 13-acetate (PMA) and 2 μM ionomycin (Iono). To assure that protein synthesis was completely suppressed throughout the course of the experiment, extra doses of CHX were added at 8, 24 and 48 h after stimulation. In parallel samples, 1 μM of the covalent proteasome inhibitor epoxomicin was added to cells 30 min before the initial CHX treatment to inhibit proteasomal degradation Approximately $10^7$ cells were collected at each time point (1, 2, 4, 8, 24, 48 and 72 h) after CHX treatment and whole cell lysates prepared as described above. Protein content was analyzed by quantitative immunoblotting using the Li-COR Odyssey infrared imaging system.

Synthesis and purification of peptides: Peptides were synthesized according to general protocols of Solid Phase Peptide Synthesis using Fmoc chemistry as described previously (Liu et al., J Am Heart Assoc. 2013; 2:e000093). Peptide sequences were verified by MALDI mass spectroscopy in the Vanderbilt Mass Spectrometry Research Core.

Importin binding assays: Biotin-labeled peptides were incubated overnight with whole-cell lysates and analyzed as described previously. For competition binding assays, non-biotinylated N50 peptide (at 0, 10, 30, 100, or 300 μM) was incubated overnight with 1.5, 0.3 or 0.05 mg/mL total protein of Jurkat T cell lysate in equivalent volumes, followed by pull-down of remaining unbound proteins with biotinylated N50 peptide immobilized on streptavidin (SA) beads Proteins were analyzed by quantitative immunoblotting.

Relative abundance of importins in human cells: An equal volume of whole cell lysate from each cell type, normalized by total protein concentration, was analyzed by quantitative immunoblotting with a panel of anti-importin antibodies Fold abundance is expressed as a ratio of corresponding band intensity normalized to GAPDH.

Preparation of plasmids, expression and purification of recombinant proteins: Plasmids for expression of recombinant glutathione S-transferase (GST) and COOH-terminal GST-tagged fusion proteins were prepared by standard cloning procedures using the pET-21a(+) vector. The $NH_2$ terminal importin beta binding (IBB) domain (aa 1-100) was deleted in constructs for human Imp α1 and Imp α5. Construct sequences were verified in the Vanderbilt Genome Sciences Research Core.

Plasmid constructs for GST-tagged Imp α1 ΔIBB, GST-tagged Imp α5 ΔIBB and GST alone were transformed into an RIL strain of BL21 (DE3) E. coli for expression. Protein expression was induced at 37° C. with 0.5 mM isopropyl β-D-2-thiogalactopyranoside for 3 h.

GST-tagged Imp α1 ΔIBB and Imp α5 ΔIBB proteins were expressed as inclusion bodies and isolated with Bugbuster Protein Extraction Reagent (Novagen) according to the manufacturer's recommendation, then solubilized in 6 M guanidine buffer (6M GuHCl, 100 mM $NaH_2PO_4$, 10 mM Tris HCl, pH 8.0) and refolded at 4° C. by dialysis against refolding buffer [1 M urea, 50 mM glycine, 20 mM HEPES (pH 8.5), 150 mM NaCl, 5 mM KCl, 2 mM $MgCl_2$, 1 mM EDTA, 2 mM GSH and 0.2 mM GSSG], followed by dialysis against FPLC Bind/Wash buffer [140 mM NaCl, 2.5 mM KCl, 10 mM $Na_2HPO_4$, 2 mM $KH_2PO_4$ (pH 7.3), 2 mM DTT, 0.01% Tween 20].

The control protein, GST, was expressed as a soluble protein. The bacterial cell pellet was resuspended on ice in FPLC Bind/Wash buffer (15 mL/g) supplemented with bacterial protease inhibitors. DNAse and lysozyme, then lysed by sonication and centrifuged to remove cell debris.

All proteins were purified by FPLC on GST affinity columns according to manufacturer's protocols and dialyzed against "intracellular" buffer [140 mM KCl, 10 mM NaCl, 10 mM Hepes (pH 7.0), 2.5 mM $MgCl_2$, 1 mM EGTA, 1 mM DTT, 0.02% NP-40, and 0.01% fatty acid-free BSA].

Determination of binding affinity: Peptide-protein binding affinity was determined based on the Bio-Layer Interferometry (BLI) technique utilized in die Octet RED96 System (ForteBio). Briefly, biotinylated N50 or N50M peptide (5 nM in PBS supplemented with 0.02% NP-40 and 0.01% fatty acid-free BSA) was immobilized on SA biosensors (10 min at 37° C.). Biosensors were washed in "intracellular" buffer (see Preparation of recombinant proteins for composition) then placed into target protein or GST control protein solutions at varying concentrations (50, 100, 150, and 200 nM). Peptide-protein interaction responses were recorded for 15 minutes, then protein solutions were replaced with "intracellular" buffer and dissociation responses recorded for an additional 15 min. Association and dissociation curves were analyzed with ForteBio Data Analysis software v. 6.3.0.40.

In silico 3-dimensional docking models: AutoDock Vina was used to generate all docking models in this study.

Generation of 3-dimensional (3-D) coordinates of ligands: Structures of QRKRQK (SEQ ID NO: 31), QRDEQK (SEQ ID NO: 32), and KKKRKVE (SEQ ID NO: 33) ligands were built from E-amino acids using the biopolymer editor in ChemBioDraw Ultra 13.0 and converted to 3-D models using ChemBio3D Ultra 13.0 software. 3-D models were then optimized by energy minimization and their coordinates saved as .pdb files.

Receptors: Three-dimensional coordinates of corresponding receptors (importins/karyopherins alpha) were obtained from the RCSB Protein Data Bank (The Research Collaboratory for Structural Bioinformatics) as PDB-formatted files. 1q1sC.pdb (crystal structure of mouse KPNA2/Imp α1). 3feyC.pdb (crystal structure of human KPNA2/Imp α1), and 3tj3B.pdb (crystal structure of human KPNA1/imp α5).

Preparation of ligand and receptor input files: Input files in PDBQT format were prepared in AutoDockTools 1.5.6 (part of the MGL Tools software package) according to a general protocol.

Docking parameters: In general, the default values for docking parameters were used except for exhaustiveness and numbers of modes, which were set to 30 and 20, respectively. Grid spacing was set at 1 Å and the size of the docking grid was determined separately for each of the major and minor importin alpha NLS binding pockets. 1q1sC—major 24 Å×32 Å×34 Å, minor 22 Å×34 ∈×34 Å; 3feyC—major 22 Å×26 Å20 Å, minor 22 Å×26 Å×20 Å; 3tj3B—major 20 Å×16 Å×28 Å, minor 22 Å×20 Å24 Å. Six independent docking models generated by AutoDock Vina were then processed, analyzed and visualized in Python Molecule Viewer 1.5.6 (PMV, part of the MGL Tools software package).

Figure 1:
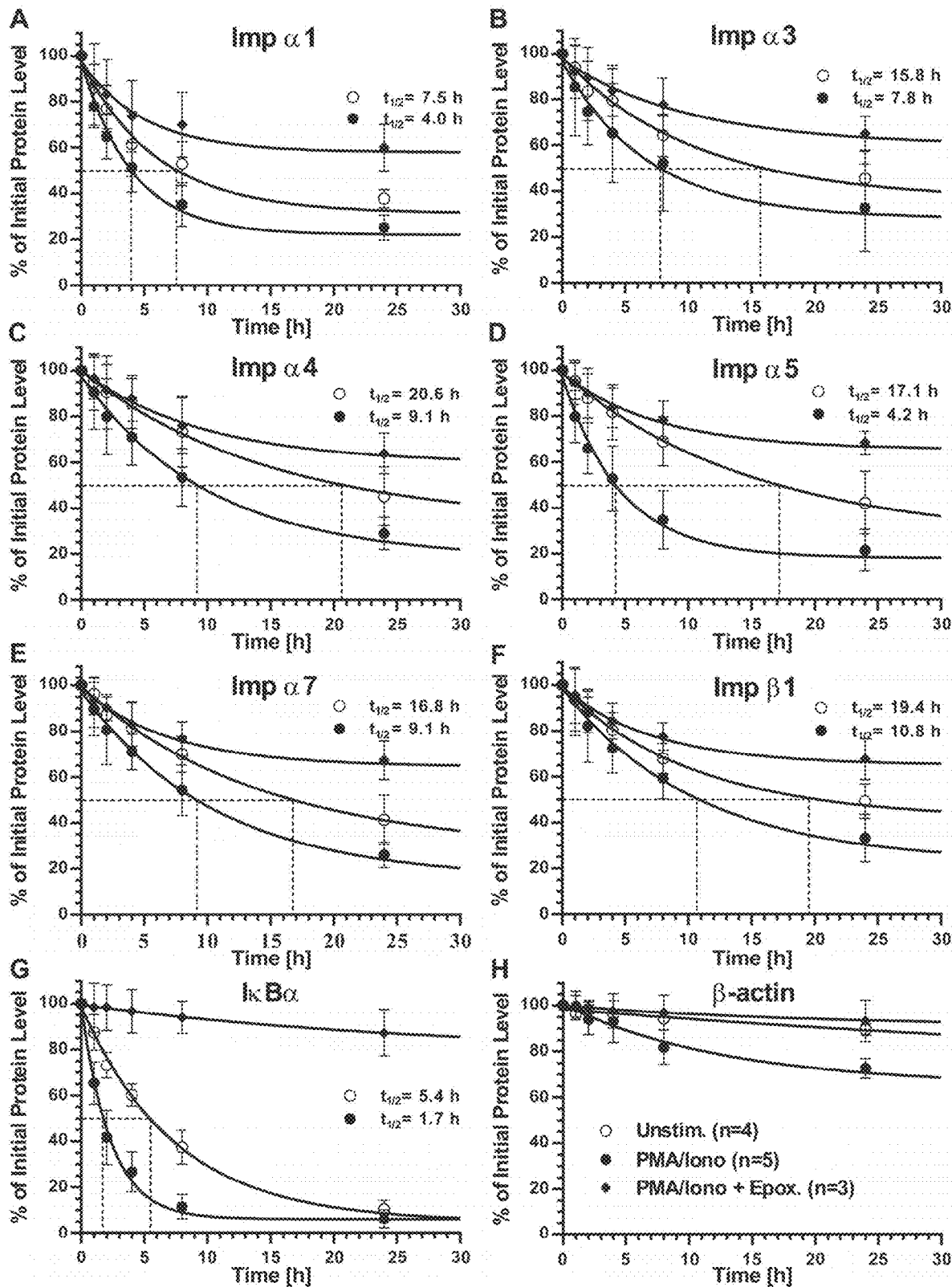
FIG. 1 shows that intracellular half-life (the $t_{1/2}$) of endogenous importins in human Jurkat T cells is regulated by proteosomal degradation. Graphic representation of quantitative immunoblot analyses of A, Imp α1; B, Imp α3; C, Imp α4, D, Imp α5; E, Imp α7; F, Imp β1; G, IκBλ, and H, β-actin in whole cell lysates from human Jurkat T cells. Cells were left unstimulated (open circles), stimulated with PMA/Iono (solid circles), or stimulated with PMA/Iono after pretreatment with the proteasome inhibitor epoxomicin (solid diamonds). Please see panel H for symbol key. All cells were first pretreated with cyclohexamide to block de novo protein synthesis Protein levels were quantified by immunoblotting and values at each time point normalized to β-actin at that same time point, then calculated as a percentage of endogenous protein at $t_0$. Dotted lines indicate $t_{1/2}$ Results are shown as the mean±SD of at least 3 independent experiments Whereas importins alpha and beta differ in their intracellular turnover in unstimulated and stimulated T cells this process depends in part on proteosomal degradation that can be attenuated by proteosome inhibitor epoxomycin
Figure 4:
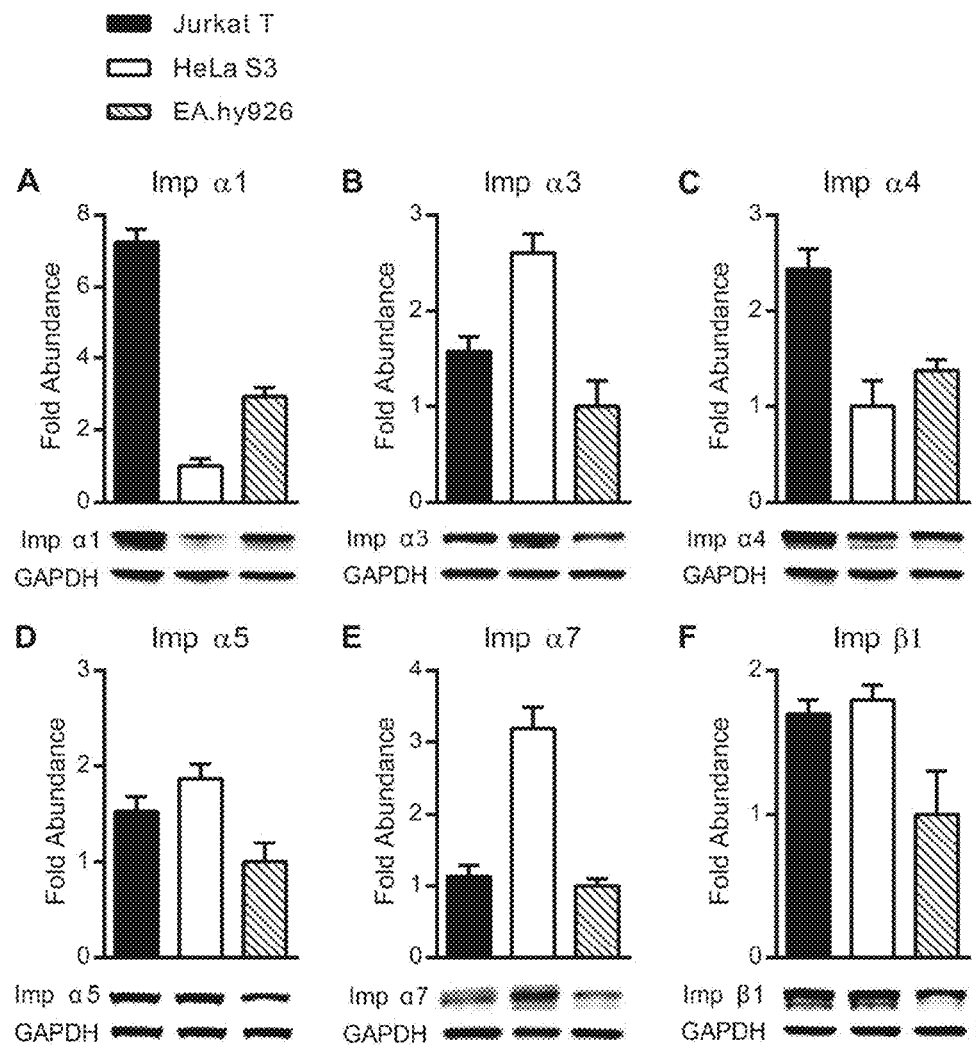
FIG. 4 shows that endogenous importins differ in their relative abundance in three different human cell lines (Jurkat T cells, HeLa S3 cells and EA.hy926 cells) A-F Endogenous proteins in whole cell lysates from unstimulated cells were analyzed by quantitative immunoblotting and the abundance of each was calculated after normalization to GAPDH controls. For each importin, the cell type with the least abundance of that importin was set to 1.0 and the relative fold abundance of this importin in the remaining cell types is indicated. The same amount of total lysate protein from all 3 cell types was used for analysis, but was adjusted empirically for each importin based on general abundance of that importin as well as its antibody sensitivity. A, Imp α1, 6 µg; B, Imp α3, 23 µg; C, Imp α4, 17 µg; D, Imp α5, 34 µg; E, Imp α7, 23 µg, and F, Imp β1, 34 µg of total lysate protein was loaded for each cell type. Results are shown as the mean+SD from 3 independent experiments.
Figure 5:
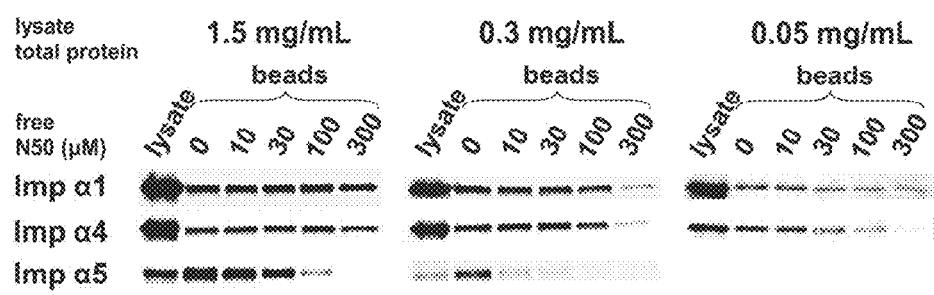
FIG. 5 shows that the N50 peptide representing NLS cargo demonstrates specific binding to Imp α5 in a competition binding assay. Unlabeled N50 peptide (free N50) at indicated concentrations was added to whole cell lysates from Jurkat T cells Biotinylated N50 peptide immobilized on agarose beads was added to pull down any importins not already complexed with free N50. Importins bound to beads were then quantified by immunoblotting A. Immunoblots of importins pulled down from lysate total protein concentrations of 1.5, 0.3 and 0.05 mg/ml. Detection of importins in whole cell lysate is shown in the first column (lysate) for comparison to importins pulled down (beads). B, Quantitative representation of immunoblots front lysate total protein concentration of 1.5 mg/ml. The value of each importin bound to beads with no competition (0) was set to 100% and the percent of remaining importins bound after competition was calculated at each concentration of free N50 and shown as the mean±SD of three independent experiments. Please note that even high concentrations of free N50 peptide do not substantially inhibit binding of Imp α1 (open circles) or Imp α4 (open diamonds) to immobilized N50, but inhibition of Imp α5 (open triangles) binding to immobilized N50 is concentration dependent.
Figure 5:
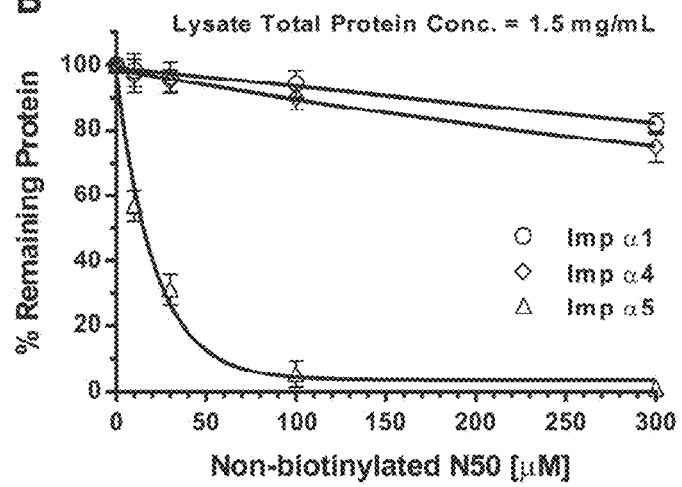

Statistical Considerations: No comparisons of treatment-induced change were implemented in any experiments included herein, therefore no formal statistical analyses were appropriate. In FIG. 1 (half-life), each corresponding data point across all panels (A through H) originates from the same cell lysate sample for each independent experiment, analyzed by immunoblotting for the different proteins. Data to generate graphs in FIG. 4 (Relative Abundance, panels A through F) was obtained from one sample for each of the three cell types for each experiment, analyzed by immunoblotting for the different proteins. All data points in FIG. 5B (Competition Binding Assay) were generated from the same cell lysate for each independent experiment, diluted and incubated with different concentrations of unlabeled peptide then immunoblotted for 3 different importins. No repeated measurements were conducted in these experiments. All data points in FIGS. 1, 4 and 5B are shown as the mean value of at least three independent experiments. To indicate the measure of sampling variability between experiments, errors are expressed as standard deviations.

Results

Figure 2:
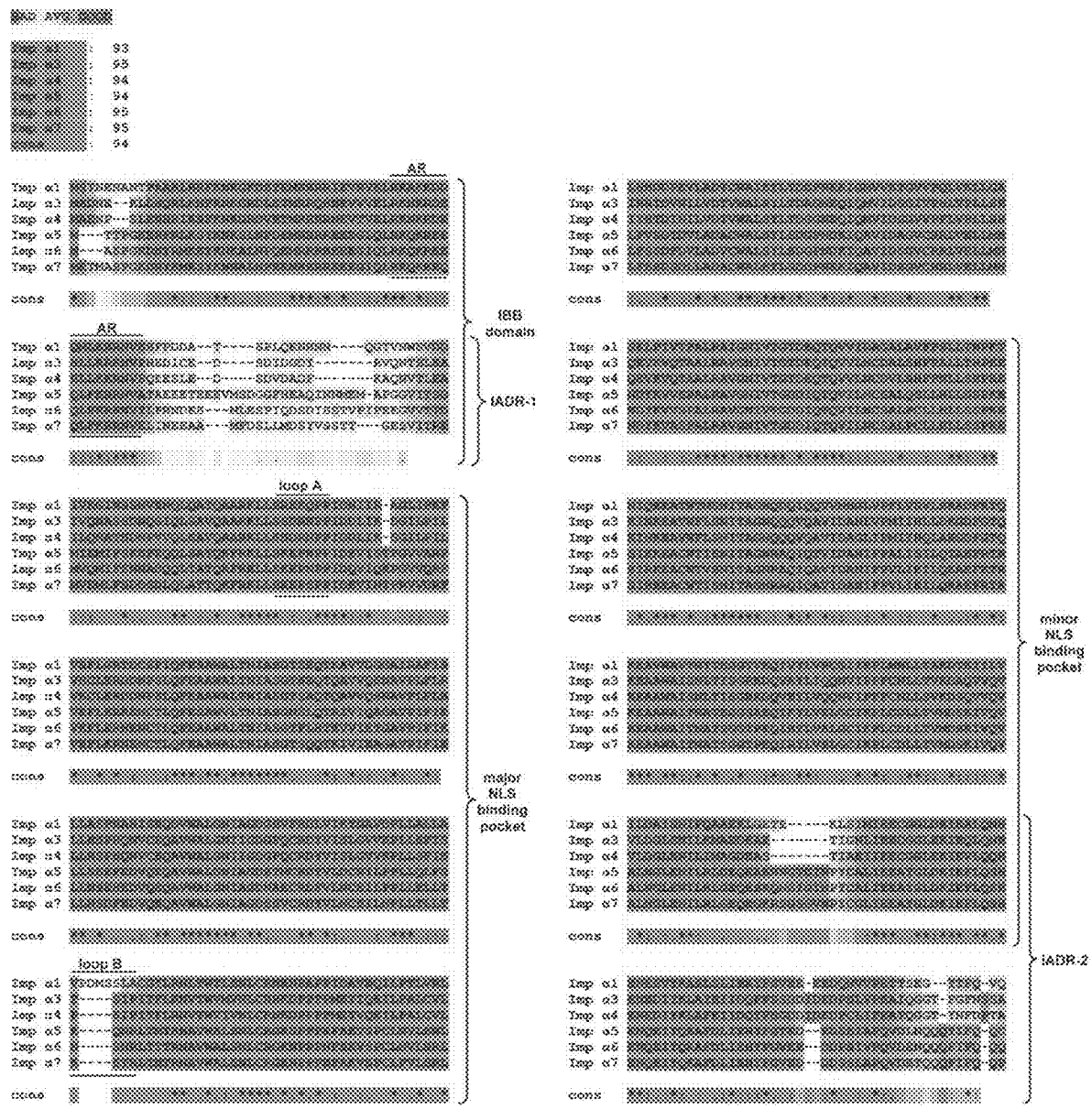
FIG. 2 shows a sequence alignment of human imponins/karyopherins alpha (SEQ ID NOS 41-46, respectively, in order of appearance) that demonstrates two Importins Alpha Diversity Regions (IADRs). Multiple sequence alignment of the importin alpha family proteins by T-Coffee software, displayed as a "heat map". Regions with a high degree of similarity are shown in red, with decreasing similarity indicated from orange to blue (see key at top). The overall similarity between different proteins is shown immediately below the color key, followed by the individual sequence alignments. The graphic colored output indicates the level of consistency between the final alignment and the library used by T-Coffee. The main score is the total consistency value A value of a 100 means full agreement between the considered alignment and its associated primary library. Please note the two regions of sequence divergence, denoted Importin Alpha Diversity Regions (IADRs), positioned near the beginning and end of the sequences. IADR-1 and IADR-2 are adjacent to, or overlap, the major and minor NLS binding pockets, respectively. Also indicated are the positions of the auto-inhibitory region (AR) within the importin beta binding (IBB) domain, and loops A and B within the major NLS binding pocket Symbol key: "cons" represents the consensus sequence, represents the same amino acid at a given position in all proteins, represents highly similar residues at a given position, and represents amino acids with a similar functionality at a given position.

Turnover of endogenous importins differs in unstimulated and stimulated human T cells. The abundance of importins contributes to their function as nuclear shuttles (Timney et al., J Cell Biol. 2006; 175:579-593). However, the intracellular turnover of endogenous importins in human cells, which contributes to their level of expression, remained unknown. Therefore, we first analyzed turnover of importins in resting and stimulated human Jurkat T cells We employed the human T lymphocyte-derived Jurkat T cell line for these analyses of endogenous importins T cells are involved in vascular inflammation caused by microbial, autoimmune, and metabolic insults, and were used in our initial study of nuclear transport of proinflammatory SRTFs. Levels of endogenous importins were determined by quantitative immunoblotting with monospecific antibodies for human Imp α1, α3, α4, α5, α7 and β1. Of the 7 known importin alpha family members, only Imp α2 and α6 were not included in our study as Imp α2 is not expressed in mammalian cells and no monospecific antibody against Imp α6 was commercially available. As shown in FIG. 1, turnover studies indicated that the $t_{1/2}$ of importins ranged between 7.5 and 20.6 h in unstimulated T cells. Upon stimulation of Jurkat T cells with PMA/Iono, standard T cell agonists that induce signal-dependent nuclear transport of SRTFs (Torgerson et al., J Immunol 1998; 161:6084-6092), the turnover of importins was accelerated (FIG. 1A-F). As a comparative control for our experimental system, we also determined the turnover of IκBα (FIG. 1G), an inhibitor of NFκB known for its stimulus-dependent accelerated turnover IκBα sequesters NFκB1-RelA heterodimers in the cytoplasm by shielding their NLSs. When inflammatory signaling is induced. IκBα is rapidly degraded by proteasomes in an ATP-dependent manner. The turnover of all proteins was normalized to turnover of the cellular control protein β-actin, which was reduced by less than 10% (in unstimulated cells) during the experimental time span used for these analyses (FIG. 1H). In most cases, importin turnover increased approximately two-fold in stimulated cells. However, the turnover of Imp α5 was accelerated four-fold (FIG. 1D), notably similar to the increased rate of turnover for IκBα (FIG. 1G). As IκBα turnover is regulated by phosphorylation, ubiquitination, and ATP-dependent proteosomal degradation, we pretreated cells with epoxomicin, an irreversible covalent inhibitor of proteasomes. As anticipated, epoxomicin drastically slowed turnover of IκBα (FIG. 1G). Significantly, it had a similar effect on turnover of all importins analyzed by us, indicating their sensitivity to proteosomal degradation (FIG. 1A-F). A search for potential protease cleavage sites in all 6 human importins using PeptideCutter software did not reveal any obvious differences between Imp α5 and other importin alpha isoforms. However, a multiple sequence comparison of all members of the human importin alpha family using T-Coffee software identified two areas of significant sequence dissimilarity, which we termed Importin Alpha Diversity Regions (IADRs), localized adjacent to the major and minor NLS binding pockets (FIG. 2).

A peptide mimicking the NF kappa B1/p50 nuclear localization sequence interacts with Imp α1, α3, α4 and α5 in three human cell types. To evaluate the mechanism of recognition specificity of human importins alpha toward NTMs, we designed studies with the knowledge that the interaction of importins alpha with nuclear cargo displaying an NLS is dependent on their cytoplasmic concentration as well as the binding affinity between them Therefore, we analyzed lysates from untransfected human cells, retaining their proteome that comprises a physiological mix of endogenous importins and other intracellular proteins to maintain their natural relative abundance and avoid potential pitfalls related to forced expression of proteins.

Figure 3:
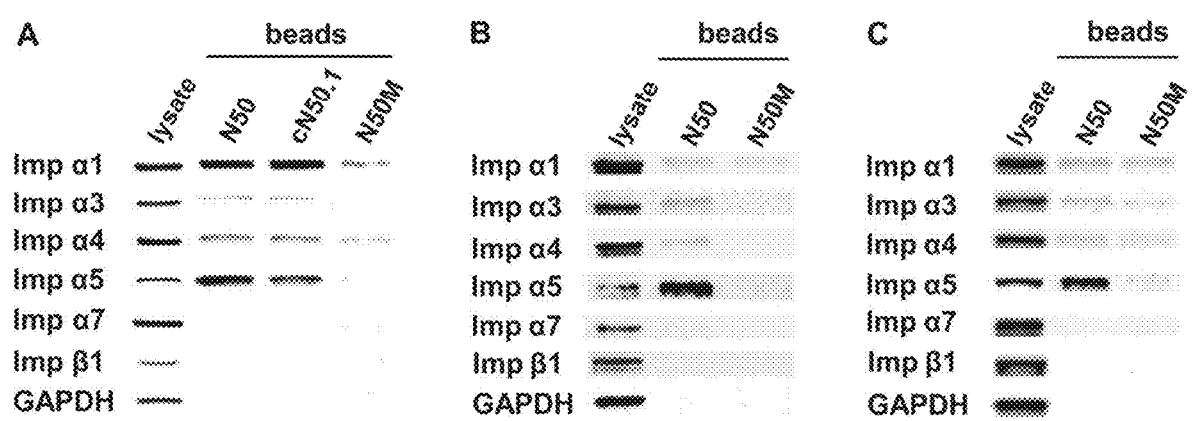
FIG. 3 shows that binding of N50 peptides representing NLS cargo to endogenous importins displays variations between different human cell types. Biotinylated N50, cN50.1 and N50M peptides (A) or N50 and N50M peptides (B and C) were added to whole cell lysates from thre distinct human cell types: A, Jurkat T cells; B. HeLa S3 epithelial cells; or C, EA.hy926 endothelial cells Peptide/protein complexes were isolated with SA-coated beads and analyzed by immunoblotting with antibodies against a panel of importins. Immunoblotting for the cellular protein GAPDH was used as a control to detect non-specific interactions. Detection of endogenous proteins in the whole cell lysate is shown in the first column (lysate).

Three NLS-based peptides mimicking the NFκB1/p50 NLS region were designed and produced for these binding studies: linear (N50), cyclized (cN50.1), and mutated (N50M) (Table 2). Peptides were labeled with biotin at the $NH_2$ terminus and a five glycine connector was added between the NLS sequence and biotin to prevent steric hindrance upon binding to SA-coated agarose beads Interaction of these peptides with endogenous nuclear import adaptor proteins was studied in three human cell types: T lymphocytes (Jurkat T cells), epithelial cells (HeLa S3), and endothelial cells (EA.hy926) to determine whether cell lineage influences the combinatorial mix of importins/karyopherins alpha interacting with NLS peptides. Peptides were incubated with whole cell lysates from unstimulated cells and complexes formed between them and cellular proteins were then captured with SA-coated beads followed by immunoblot analysis with antibodies to Imp α1, α3, α4, α5, α7, β1 and GAPDH. The avidity of peptide/protein interactions shows a similar pattern in all 3 cell types (FIG. 3). Four out of the 6 analyzed importins, Imp α1, α3, α4 and α5, were detected in association with N50 and cN50.1 peptides. The remaining two importins, Imp α7 and Imp β1, although present in the lysate, were not pulled down by any of the peptides in any cell type. The mutated control peptide, N50M, was slightly reactive, as only weak interactions were observed between N50M and Imp α1 and α4, and interaction with Imp α5 was barely detectable (FIG. 3).

While differing antibody specificities preclude quantitative comparisons between different importins, using the same antibody to detect a given importin in lysates from three different cell types accurately reflects its relative abundance in different cell types (FIG. 4), and demonstrates the variable strength of peptide/protein interactions. Likewise, the ratio between the amount of an individual importin pulled down by binding to N50 compared to the amount of that importin detected in the lysate fraction defines the relative strength of N50 binding to that importin. Thus, we determined that interaction between N50 peptide and Imp α1 is weaker in lysates from HeLa S3 cells (FIG. 3B) and EAhy926 cells (FIG. 3C) as abundance of these proteins is 7 and 2 fold lower, respectively, compared to Jurkat T cells (FIG. 4A). A similar pattern is observed when N50 peptide interacts with Imp α4. This interaction appears stronger in the lysate obtained from Jurkat T cells (FIG. 3A) compared to the same interaction in HeLa S3 cells (FIG. 3B) and EA hy926 cells (FIG. 3C) as abundance of Imp α4 is two-fold higher in Jurkat T cells than in the other two cell lines (FIG. 4C). In contrast, interaction of N50 peptide with Imp α3 is stronger in HeLa S3, as its abundance in this cell line is two-fold higher (FIG. 4B). Imp α7 follows a similar pattern to Imp α3 (FIG. 4E). The interaction of N50 peptide with Imp α5 is similarly strong in all three cell types, consistent with comparable intracellular concentrations of this importin (FIG. 4D) and akin to the pattern seen with Imp β1 (FIG. 4F) Nonetheless, the relative amount of Imp α5 bound to biotinylated N50 pulled down by SA-coated beads is strikingly higher than any of the other detected proteins, indicating that the interaction between N50 and Imp α5 is stronger than the other peptide/protein interactions analyzed in this study. Based on this observation, we focused our next experiments on defining the specificity of N50 interactions with Imp α5 in competition binding assays compared to N50 interactions with Imp α1 and α4.

Specificity of peptide binding to importins alpha. The results from the importin binding assay led us to postulate that interactions between N50 and Imp α5 were more specific than those with Imp α1 and α4. Therefore, we designed a modified competition binding assay to determine specificity of N50 binding to different importins. We added increasing concentrations of unlabeled "free" N50 peptide to different concentrations of lysate total protein from unstimulated Jurkat T cells. After overnight incubation at 4° C. biotinylated N50 peptide, immobilized on SA beads, was added to pull down unbound proteins, which were then detected by quantitative immunoblotting (FIG. 5A). Binding of Imp α5 to immobilized N50 peptide was tightly controlled by unlabeled peptide in all lysate total protein concentrations. In the most concentrated lysates (1.5 mg/mL), approximately 70% inhibition was observed with 30 μM of unlabeled peptide and about 95% inhibition with 100 μM. In striking contrast, binding of Imp α1 and α4 to immobilized N50 peptide in the most concentrated extracts was slightly inhibited. Imp α1 and α4 band intensities were only reduced by about 20% with the highest concentration of unlabeled peptide (300 μM) (FIG. 5B). Their relatively unchanged binding isotherms, especially compared to the dramatic inhibition of Imp α5 in the most concentrated lysate (FIG. 5B), provided additional evidence that N50 interactions with Imp α1 and Imp α4 are non-specific.

Figure 6:
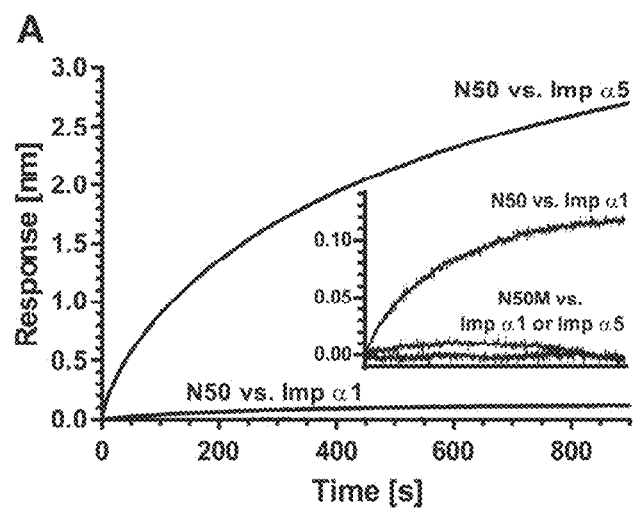
FIG. 6 shows that N50 peptide displays high binding affinity for Imp α5, but not Imp α1 in a Bio-Layer Interferometry assay Biotinylated N50 or its non-binding mutant control N50M immobilized on SA-coated biosensors were incubated at 30° C. with 50, 100, 150 or 200 nM solutions of GST-tagged Imp α1 ΔIBB, GST-tagged Imp α5 ΔIBB or GST alone. A. Association curses of N50 peptide with Imp α1 at 200 nM and with Imp α5 at 200 nM, normalized by subtracting N50 peptide binding with GST at 200 nM. Association curves of N50M mutant peptide with Imp α1 and Imp α5, both at 200 nM, normalized by subtracting N50M mutant peptide binding with GST at 200 nM are shown in the inset panel, along with the binding isotherm for N50 peptide with Imp α1 at 200 nM, for comparison. B. Fitting curves corresponding to a 1:1 (upper) or 2:1 (bottom) binding stoichiometry for interaction between N50 and Imp α5 Exp=recorded signal (heavy solid line), Fit=simulation curve (dotted line), Res=residual curve (thin solid line, Exp minus Fit). Each graph is representative of three independent experiments. Binding affinities were calculated using data from all concentrations of GST proteins in all 3 experiments.
Figure 6:
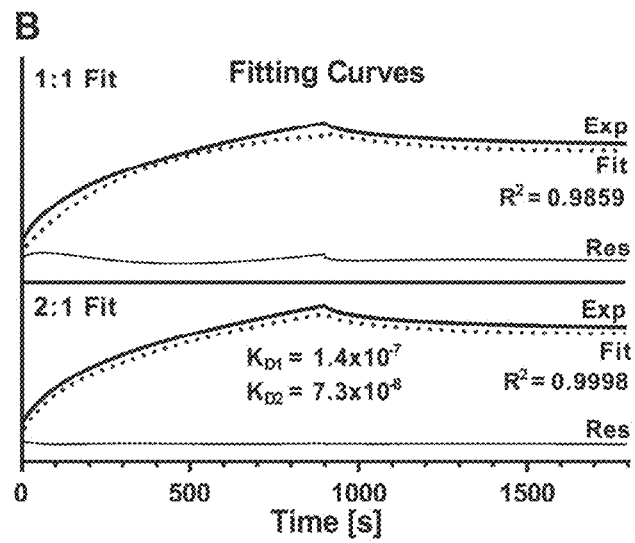

Interaction of N50 peptide with Imp α5 shows strong binding affinity with 2:1 stoichiometry. Having established the specificity of N50 peptide binding to Imp α5, we set out to determine the strength of this interaction, as compared to the interaction with Imp α1, by performing binding affinity assays using GST-tagged importin alpha proteins produced without their NH2-terminal importin beta binding (IBB) domains, which contain an auto-inhibitory region (AR) that prevents non-specific cargos from interacting with their major and minor NLS binding pockets (see FIG. 2). Biotinylated N50 peptide was immobilized on SA biosensors and incubated with GST-tagged Imp α1 ΔIBB and Imp α5 ΔIBB, at 50, 100, 150 and 200 nM concentrations Biotinylated N50M peptide served as an inactive peptide control, and solutions of GST alone at corresponding concentrations were used as background control. Consistent with previous experiments showing binding specificity (sec FIG. 5), the maximum response recorded for interaction of N50 peptide with Imp α5 was more than 20 fold higher than the maximum response recorded during interaction of N50 peptide with Imp α1 (FIG. 6A). The responses obtained using control mutant peptide. N50M, as a ligand for interaction with Imp α5 and α1 proteins were both at the background level (FIG. 6A, inset).

Detailed analysis of this data indicated that interaction between N50 peptide and Imp α5 most likely proceeds according to a 2:1 kinetic model (FIG. 6B). Fitting the theoretical curve with the experimental data in the 2:1 model resulted in a correlation coefficient equal to $R^2=0.9998$ and a flat residual curve, while fitting in the 1:1 model gave $R^2=0.9859$, resulting in an irregular-shaped residual curve. The binding affinities in the 2:1 model were calculated as $K_{D1}=1.4\times10^{-7}$ M and $K_{D2}=7.3*10^{-8}$ M (FIG. 6B). Cumulatively, these results indicate preferential and specific binding of N50 peptide to Imp α5 whereas the observed binding to Imp α1 was proven non-specific. The 2:1 stoichiometry of the N50 peptide binding to Imp α5 suggests occupancy of both major and minor NLS binding pockets on Imp α5.

Figure 7:
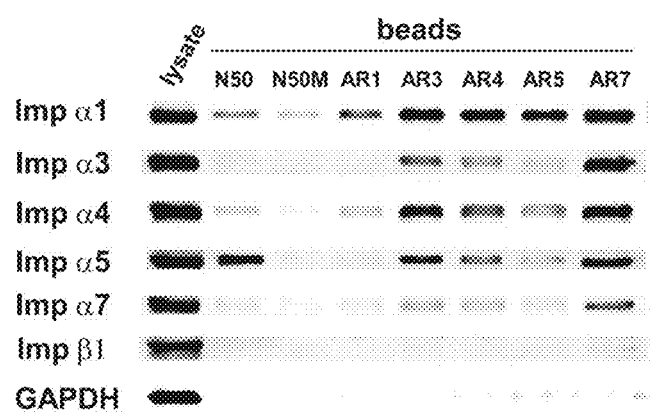
FIG. 7 shows that auto-inhibitory region (AR) of Importin alpha 7 is the most specific for its cognate importin shielding it from other ARs and N50 peptide whereas autoinhibitory region of importin alpha 1 is the least protective allowing binding of multiple peptides. Biotinylated N50 and N50M peptides, as well as biotinylated peptides representing the ARs of Imp α1, α3, α4, α5 and α7, were added individually to whole cell lysates from Jurkat T cells. The peptide and its interacting proteins were pulled down with SA-coated beads and analyzed by immunoblotting with antibodies against a panel of importins as in FIG. 3. Immunoblotting for the cellular protein GAPDH was used as a control to detect non-specific interactions Detection of endogenous proteins in the whole cell lysate is shown in the first column (lysate).

The auto-inhibitory region of Imp α7 impedes N50 peptide access to its NLS binding pockets. Given the high degree of homology between Imp α5 and Imp α7 (see Table 3B), we were puzzled by our inability to detect any interactions between N50 and endogenous Imp α7 in binding assays (see FIG. 3). We hypothesized that the auto-inhibitory effect of ARs differs among endogenous importins alpha, thereby affecting the ability of N50 peptide to access NLS binding pockets. To test this hypothesis, we designed and produced biotinylated peptides derived from the ARs of each importin alpha (see Table 2) and employed them in binding assays in human T cell lysate to determine their ability to compete with native AR homologs. As shown in FIG. 7, the protective effect of ARs does vary among the different importins alpha Imp α1 displayed the least protection by its AR, which was unable to efficiently protect its NLS binding pockets from interaction with any biotinylated ligands (row 1), or compete with native ARs to bind other importins (column 4). Conversely, Imp α7 was most protected by its AR, as most of the biotinylated peptides displayed minimal interaction with endogenous Imp α7 (row 5). Moreover, biotinylated AR7 successfully competed with native ARs of all importins alpha, including its own (column 8). These results indicate that the binding affinity of the Imp α7 AR to its own major and minor NLS binding pockets is stronger than the affinity of the N50-Imp α7 interaction, thus explaining the inability of biotinylated N50 peptide to pull down Imp α1 (see FIG. 3).

Models of N50 peptide docking to Imp α1 and α5 confirm their different binding characteristics. We employed 3-D models of NLS-Imp α docking to identify structural elements of importins alpha potentially responsible for stabilization/destabilization of observed interactions with N50. All docking models were generated by AutoDock Vina software using available crystal structures of human Imp α1 (PDB ID 3FEY Chain C) and human Imp α5 (PDB ID 3TJ3 Chain B). Since the crystal structure of the NFκB/p50 NLS was not available, we used ChemOffice 13.0 software to build, optimize and generate 3-D coordinates of peptide chains to serve as ligands in our docking model Before attempting an in silico docking analysis of p50 NLS peptide to Imp α1 and α5, we first verified the accuracy of the AutoDock Vina software by performing a control docking analysis using a binding pair that has been previously analyzed by X-ray crystallography, and therefore has an independently verified binding conformation.

Figure 8:
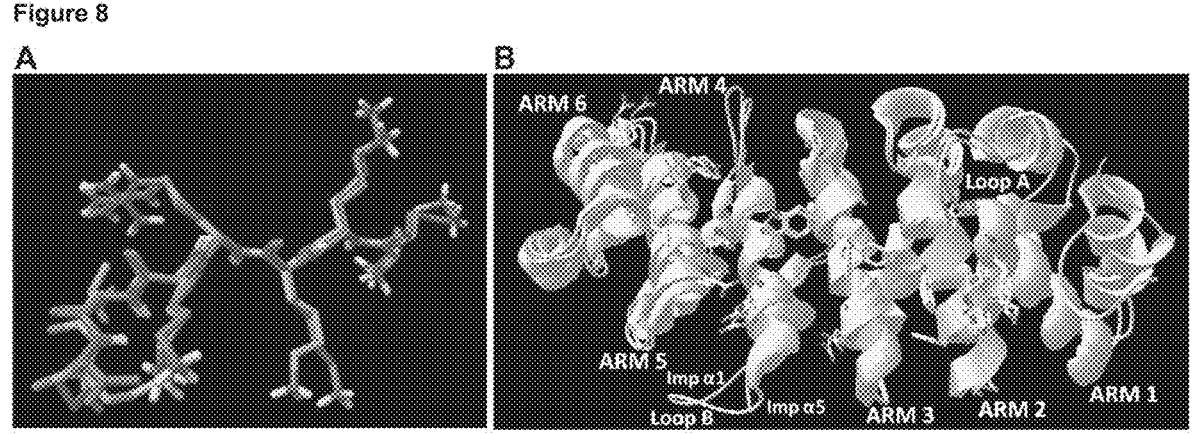
FIG. 8 shows three-dimensional models of NLS from SV40 virus and superimposed ribbon structures of of the major NLS binding pockets of importins alpha 1 and 5. A, Unaligned images of the conformation of SV40 NLS obtained from the control modeling of its interaction with mouse Imp α1 (orange) and the structure of the same NLS motif obtained from X-ray Crystallography (PDB ID 1Q1SChain B) (green) are shown overlapped Functional atoms are color coded: red—oxygen, blue—nitrogen, white—polar hydrogen. The RMSD of alpha carbons and all backbone atoms of unaligned conformations equals 0.58 Å and 0.77 Å, respectively. When aligned, the RMSD of alpha carbons and all backbone atoms equals 0.36 Å and 0.56 Å, respectively Conformation of SV40 NLS were generated by AutoDock Vina 1.1.2 and visualized in PythonModelViewer 1.5.6 B. Imp α1 and α5 structures display high homology. Superimposed ribbon structures of the major NLS binding pockets from human Imp α1 (KPNA2, PDB ID 3FEY Chain C) and human Imp α5 (KPNA1, PDB ID 3TJ3 Chain B). The positions of structural components, including the major functional residues on the surface of NLS binding pockets, indicate a high degree of structure and sequence similarity. Loop B was identified as a region of structural diversity, in addition to IADR-1 and IADR-2 (See FIG. 2). Structures were visualized in DeepView software (Swiss-PdbViewer 4.1.0, Swiss Institute of Bioinformatics).

We selected a crystal structure of simian-virus-40 large T-antigen (SV40) NLS bound to mouse Imp α1, available at RCSB Protein Data Bank (PDB ID: 1Q1S). For practical reasons, we reduced the length of the SV40 NLS sequence to 7 residues: KKKRKVE (SEQ ID NO: 33) (42 rotatable bonds), then generated 3-D coordinates and modeled its docking to the major NLS binding site of mouse Imp α1 (PDB ID 1Q1S Chain C). The resulting ligand conformations were analyzed in PythonMoleculeViewer (PMV) and compared to the known crystal structure of this NLS (PDB ID 1Q1S Chain B). We identified a conformation that was highly similar to its crystallographic homolog (FIG. 8A), confirming the capability of the software to generate accurate docking models. The root mean square deviation (RMSD) of alpha carbons and all backbone atoms equaled 0.36 Å and 0.56 Å, respectively.

After the accuracy of the software was established, we used the strict NLS sequence of N50 peptide (QRKRQK) (SEQ ID NO: 31) as a ligand to model docking to the major and minor NLS binding pockets of Imp α1 and α5. This sequence corresponds to the NLS sequence of NFκB1/p50. As a control ligand, we used an inactive loss-of-function mutant of this NLS (QRDEQK) (SEQ ID NO: 32), corresponding to the mutated sequence of N50M (see Table 2) The 3-D coordinates of these peptide chains, each containing around 30 rotatable bonds, were generated as described in the Methods, and adapted as ligand files using AutoDockTools software. The docking models were obtained through 4 independent processes, individually covering binding to major and minor NLS binding pockets of each importin alpha. Conformations with the best binding affinity (lowest binding energy) were chosen for further analysis. Results showing docking of QRKRQK (SEQ ID NO: 31) and its mutant QRDEQK (SEQ ID NO: 32) sequences to both NLS binding pockets of Imp α1 and α5 are presented in Table 4. Even though QRKRQK (SEQ ID NO: 31) sequence occupies a similar position in major NLS binding pocket of both importins (FIGS. 9C and D), analysis of docking affinities ($K_D$, calculated for T=173 K with the assumption that free rotation around the majority of bonds is frozen) indicates that its binding to Imp α5 is approximately 10 times stronger than to Imp α1 (0.6 nM and 1.9 nM versus 4.5 nM and 19 nM) (Table 4B). These calculated values are consistent with those obtained experimentally for N50 binding to Imp α5 by BLI (Table 4A). Though the high degree of similarity demonstrated in FIG. 2 between the major NLS binding pockets of Imp α1 and α5 is paralleled by their structures (FIG. 8B), the higher binding affinity of the QRKRQK (SEQ ID NO: 31) sequence to Imp α5 suggests existence of a structural element stabilizing their interaction. Despite their high homology, a comparative structural analysis of the major NLS binding pockets of Imp α1 and α5 identified an inconsistency in the structure of loop A [the loop connecting ARM1 with ARM2 (see FIG. 8B and FIG. 2)]. The central position on loop A in Imp α1 is occupied by lysine (K108) (FIG. 9A), while the same position on Imp α5 is occupied by proline (P114) (FIG. 9B), forcing the side chain of glutamic acid (E113) to bend (FIGS. 9B and D) This structural difference may stabilize a positively charged cargo bound to the Imp α5 major NLS binding pocket. The side chain of the corresponding amino acid on Imp α1, glutamate E107, projects out from the surface and does not participate in stabilization of docked cargo (FIGS. 9A and C). When the mutated QRDEQK (SEQ ID NO: 32) sequence was used as a docking ligand, binding affinity for Imp α5 to the major binding pocket decreased 25 fold and to the minor binding pocket 8 fold (15 nM for both, see Table 4C). The ligand mutation had less effect on binding affinity for Imp α1. Mutated ligand docking affinity for the major pocket decreased 3 fold, but conversely, binding to the minor site was almost 2 fold stronger (11 nM for both, see Table 4C). The lack of any significant loss in affinity by the mutated sequence for Imp α1 suggests that the surface of the NLS binding pocket on Imp α1 is more permissive, allowing negatively charged residues to bind with similar affinity. This might also explain the presence of a protein band corresponding to an N50M-Imp α1 interaction in binding assays (see FIG. 3). Thus molecular modeling based on energy minimization algorithms is fully consistent with experimentally obtained binding parameters of N50 peptide in regard to Imp α5 (high affinity) and Imp α1 (low affinity).

Discussion

Nuclear transport adaptors in the importin alpha family are highly similar (see Table 3B and FIG. 2) and each comprises 10 armadillo (ARM) repeats that form major and minor NLS binding pockets located in their NH2- and COOH-terminal regions, respectively. In this study we have determined that N50 peptide, which mimics the NLS region of NFκB1/p50, interacts in human cells with endogenous importins alpha and successfully competes with their autoinhibitory regions (ARs) for NLS binding pockets We show that variability in the protective effect of the ARs in different importin alpha family members might also play a role in their binding to the NLS represented by N50, especially in the case of Imp α7, which is inaccessible to this peptide. Importantly, we demonstrated for the first time that N50 peptide preferentially binds to Imp α5 (KPNA1) with 2:1 stoichiometry. This stoichiometry is consistent with compelling evidence provided by X-ray crystallography (Conti et al., Cell 1998; 94:193-204; Fontes et al., J Mol Biol. 2000; 297:1183-1194) and Surface Plasmon Resonance data (Catimel et al., J Biol Chem 2001; 276:34189-34198).

We also found that the turnover of importins is accelerated in stimulated T cells due, at least in part, to proteasomal degradation, mostly by the beta-5 subunit and to a lesser degree by the beta-2 subunit of proteasomes inactivated by epoxomycin. Given the essential role of ATP-dependent proteosomal degradation of IκBα, we propose that the protective effect of epoxomicin on importins turnover in stimulated cells implies a similar mechanism of proteosomal degradation. Among the six human importins studied here, Imp α5 has the twice the rate of turnover in stimulated human lymphocytes than any other importin we studied, suggesting that it may be more readily degraded by the epoxomicin-targeted beta-5 subunit of the proteasome. Accelerated turnover of Imp α5 in stimulated cells indicates that Imp α5, despite its high homology with Imp α6 and Imp α7 (Table 3B), is more prone to degradation than other importins when inflammatory signaling is induced, thereby limiting availability of Imp α5 for nuclear transport of cognate TFs. This rate-limiting mechanism may dampen excessive transport of proinflammatory transcription factors, such as STAT1, to the nucleus.

We propose that targeting Imp α5 by the N50 sequence of SN50 and its subsequent NTM congeners (cSN50 and cSN50.1) contributes to inhibition of signaling pathways evoked by metabolic, autoimmune, and microbial stimuli that cause inflammatory disorders analyzed in their preclinical models (Liu et al., J Am Heart Assoc 2013; 2:e000093). It is important to note that Imp α5-deficient mice are viable and fertile and do not show any obvious morphological or behavioral abnormalities (Shmidt et al., Nat Cell Biol. 2007; 9:1337-1338), supporting the observation in these preclinical models that in vivo targeting of Imp α5 in the nuclear import machinery by NTMs is well-tolerated (Liu et al. J Am Heart Assoc 2013; 2:e000093). Thus, these findings provide a structural and functional framework for development of the next generation of NTM peptides to preferentially target nuclear transport by different members of the importin alpha family.

TABLE 2

| Peptide | Sequence | SEQ ID NO: |
|---------|----------|------------|
| N50 | VQRKRQKLMP | 34 |
| N50M | VQRDEQKLMP | 8 |
| cN50.1 | CVQRKRQKLMPC | 35 |
| AR1 | VELRKAKKDDQMLKRRNVSSF | 36 |
| AR3 | VELRKNKRDEHLLKRRNVPHE | 37 |
| AR4 | VELRKNKRDEHLLKKRNVPQE | 38 |
| AR5 | LQLRKQKREEQLFKRRNVATA | 39 |
| AR7 | IQLRKQKREQQLFKRRNVELI | 40 |

Table 2. Amino acid sequences of peptides used in this study N50—sequence derived from the NLS region of NFκB1/p50; N50M—sequence of control peptide with KR to DE mutation (bold); cN50.1—sequence of cyclized version of N50. An intra-molecular disulfide bond is formed between the two cysteines. AR1 through AR7—sequences derived from the auto-inhibitory region (AR) of Imp α1 through Imp α7.

TABLE 3

A

| Importin | Karyopherin | Alternative Name |
|---|---|---|
| Importin alpha 1 (Imp α1) | Karyopherin alpha 2 (KPNA2) | Rch1 |
| Importin alpha 3 (Imp α3) | Karyopherin alpha 4 (KPNA4) | Qip1 |
| Importin alpha 4 (Imp α4) | Karyopherin alpha 3 (KPNA3) | SRP1γ |
| Importin alpha 5 (Imp α5) | Karyopherin alpha 1 (KPNA1) | SRP1 |
| Importin alpha 6 (Imp α6) | Karyopherin alpha 5 (KPNA5) | |
| Importin alpha 7 (Imp α7) | Karyopherin alpha 6 (KPNA6) | |
| Importin beta 1 (Imp β1) | Karyopherin beta 1 (KPNB1) | |

B

| Imp α3 | Imp α4 | Imp α5 | Imp α6 | Imp α7 | |
|---|---|---|---|---|---|
| 50 | 49 | 45 | 47 | 47 | Imp α1 |
| | 85 | 46 | 48 | 47 | Imp α3 |
| | | 48 | 49 | 47 | Imp α4 |
| | | | 80 | 81 | Imp α5 |
| | | | | 85 | Imp α6 |

Table 3. Nomenclature (A) and Sequence Identity (B) of Importins. A, Currently used nomenclatures for nuclear import adaptor proteins. Color shaded areas identify members of the three importin alpha subfamilies B, Comparison of the human importin alpha protein family sequences with sequence identity expressed as a percent of the total number of amino acids. Shaded blocks show sequence identity of subfamily members.

TABLE 4

| | Imp α1 | | Imp α5 | |
|---|---|---|---|---|
| | Major | Minor | Major | Minor |
| A. VQRKRQKLMP (SEQ ID NO: 34) | | | | |
| $K_D$ [nM] (BLI) | N/D | N/D | 73 | 140 |
| B. QRKRQK (SEQ ID NO: 31) | | | | |
| ΔG [kcal/mol] (dock) | −6.6 | −6.1 | −7.3 | −6.9 |
| $K_D$ [nM] (calc)* | 4.5 | 19 | 0.6 | 1.9 |
| C. QRDEQK (SEQ ID NO: 32) | | | | |
| ΔG [kcal/mol] (dock) | −6.3 | −6.3 | −6.2 | −6.2 |
| $K_D$ [nM] (calc)* | 11 | 11 | 15 | 15 |

*Calculated from the equation $\Delta G = RT \cdot \ln(K_D)$ for T = 173K, with the assumption that rotation around the majority of bonds is frozen.

Table 4 Characteristics of N50-Imp α interactions A. N50-Imp α binding affinity ($K_D$) obtained from Bio-Layer Interferometry (see FIG. 6), B and C, Docking energy and calculated docking affinity obtained from modeling of B, N50 and C, N50M interactions with Imp α1 and α5. Docking energy was generated by AutoDock Vina 1.1.2. Please note that docking affinities obtained from the modeling study differ from those obtained from BLI due to different experimental conditions (temperature, ligand size, etc). However, the binding characteristics are generally consistent between the 2 methods.

Other Embodiments

Any improvement may be made in pan or all of the compositions, kits, and method steps. All references, including publications, patent applications, and patents, cited herein are hereby incorporated by reference. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contraindicated by context.

What is claimed is:

1. A composition comprising a pharmaceutically acceptable carrier and an importin alpha-selective nuclear transport modifier (NTM) comprising the amino acid sequence SEQ ID NO: 19 in an amount effective for modifying entry of at least one transcription factor into a cell's nucleus.

2. A method for alleviating, relieving, altering, remedying, ameliorating, improving, or affecting inflammatory disorders and/or the signs of inflammation in a mammalian subject comprising administering to the subject a composition of claim 1.

3. The method of claim 2, wherein the composition is administered with a corticosteroid or non-steroidal anti-inflammatory agent.

4. The method of claim 3, wherein the non-steroidal anti-inflammatory agent is acetaminophen or ibuprofen.

5. The method of claim 2, wherein the composition further comprises a corticosteroid or non-steroidal anti-inflammatory agent.

6. The method of claim 5, wherein the non-steroidal anti-inflammatory agent is acetaminophen, aspirin, or ibuprofen.

7. The method of claim 2, wherein the subject has an autoimmune, metabolic, microbial, posttraumatic or neoplastic disease.

8. The method of claim 7, wherein the subject is a human.

9. A kit comprising:

a) a composition including a pharmaceutically acceptable carrier and, in an amount effective for modifying entry of at least one transcription factor into a cell's nucleus, at least one selected from the group consisting of: an importin alpha-selective NTM comprising the amino acid sequence SEQ ID NO:16, 17, 18, 19, 20, 25, 26, 27, 28, 29, or any combination thereof, wherein the importin alpha-selective NTM is a peptide that binds to one or more binding sites of an importin alpha and that modifies nuclear transport of at least one intracellular protein; and an inhibitor of an importin alpha and importin beta interaction comprising the amino acid sequence SEQ ID NO:9, 10, 11, 12, 13, 14, 15, 21, 22, 23, 24, or any combination thereof;

b) packaging; and c) instructions for use.

10. The kit of claim 9, wherein the composition further comprises an importin beta-selective NTM comprising the amino acid sequence SEQ ID NO: 2.

11. A method for alleviating, relieving, altering, remedying, ameliorating, improving, or affecting inflammatory disorders and/or the signs of inflammation in a mammalian subject comprising administering to the subject a composition comprising a pharmaceutically acceptable carrier and an importin alpha-selective NTM comprising the amino acid sequence SEQ ID NO: 16, 17, 18, 19, 20, 25, 26, 27, 28, 29, or any combination thereof, in an amount effective for modifying entry of at least one transcription factor into a cell's nucleus.

12. The method of claim 11, wherein the composition is administered with a corticosteroid or non-steroidal anti-inflammatory agent.

13. The method of claim 12, wherein the non-steroidal anti-inflammatory agent is acetaminophen or ibuprofen.

14. The method of claim 11, wherein the composition further comprises a corticosteroid or non-steroidal anti-inflammatory agent.

15. The method of claim 14, wherein the non-steroidal anti-inflammatory agent is acetaminophen, aspirin, or ibuprofen.

16. The method of claim 11, wherein the subject has an autoimmune, metabolic, microbial, posttraumatic or neoplastic disease.

17. The method of claim 16, wherein the subject is a human.

* * * * *